(12) United States Patent
Merkulov et al.

(10) Patent No.: US 6,294,368 B1
(45) Date of Patent: Sep. 25, 2001

(54) ISOLATED HUMAN METALLOPROTEASE PROTEINS, NUCLEIC ACID MOLECULES ENCODING HUMAN PROTEASE PROTEINS, AND USES THEREOF

(75) Inventors: Gennady V. Merkulov, Baltimore; Jane Ye, Boyds; Valentina Di Francesco, Rockville; Ellen M. Beasley, Darnestown, all of MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/813,819

(22) Filed: Mar. 22, 2001

(51) Int. Cl.[7] .......................................................... C12N 9/70
(52) U.S. Cl. ...................... 435/219; 435/69.1; 435/320.1; 536/23.2; 536/23.5
(58) Field of Search ................................... 435/69.1, 219, 435/320.1; 536/23.2, 23.5

(56) References Cited

U.S. PATENT DOCUMENTS 6,203,979 * 3/2001 Bandman et al. ....................... 435/6

* cited by examiner

Primary Examiner—Nashaat T. Nashed
Assistant Examiner—Christian L. Fronda
(74) Attorney, Agent, or Firm—Celera Genomics; Robert A. Millman; Lin Sun-Hoffman

(57) ABSTRACT

The present invention provides amino acid sequences of peptides that are encoded by genes within the human genome, the protease peptides of the present invention. The present invention specifically provides isolated peptide and nucleic acid molecules, methods of identifying orthologs and paralogs of the protease peptides, and methods of identifying modulators of the protease peptides.

9 Claims, 23 Drawing Sheets

```
   1  CGACCTGGCC  GCCGGCCGCT  CCTCCGCGCG  CTGTTCCGCA  CTTGCTGCCC
  51  TCGCCCGGCC  CGGAGCGCCG  CTGCCATGCG  GCTGGCGCTG  CTCTGGGCCC
 101  TGGGGCTCCT  GGGCGCGGGC  AGCCCTCTGC  CTTCCTGGCC  GCTCCCAAAT
 151  ATAGCCCTGC  TGTCGATTCC  CTCAGTACTG  TCTTGGGGTG  TCCTGGGACC
 201  TGCAGGTGGC  ACTGAGGAGC  AGCAGGCAGA  GTCAGAGAAG  GCCCCGAGGG
 251  AGCCCTTGGA  GCCCCAGGTC  CTTCAGGACG  ATCTCCCAAT  TAGCCTCAAA
 301  AAGGTGCTTC  AGACCAGTCT  GCCTGAGCCC  CTGAGGATCA  AGTTGGAGCT
 351  GGACGGTGAC  AGTCATATCC  TGGAGCTGCT  ACAGAATAGG  GAGTTGGTCC
 401  CAGGCCGCCC  AACCCTGGTG  TGGTACCAGC  CCGATGGCAC  TCGGGTGGTC
 451  AGTGAGGGAC  ACACTTTGGA  GAACTGCTGC  TACCAGGGAA  GAGTGCGGGG
 501  ATATGCAGGC  TCCTGGGTGT  CCATCTGCAC  CTGCTCTGGG  CTCAGAGGCT
 551  TGGTGGTCCT  GACCCCAGAG  AGAAGCTATA  CCCTGGAGCA  GGGGCCTGGG
 601  GACTTTCAGG  GTCCTCCCAT  TATTTCGCGA  ATCCAAGATC  TCCACCTGCC
 651  AGGCCACACC  TGTGCCCTGA  GCTGGCGGGA  ATCTGTACAC  ACTCAGACGC
 701  CACCAGAGCA  CCCCCTGGGA  CAGGCCACA   TTCGCCGGAG  GCGGGATGTG
 751  GTAACAGAGA  CCAAGACTGT  GGAGTTGGTG  ATTGTGGCTG  ATCACTCGGA
 801  GGCCCAGAAA  TACCGGGACT  TCCAGCACCT  GCTAAACCGC  ACACTGGAAG
 851  TGGCCTCTT   GCTGGACACA  TTCTTCCGGC  CCCTGAATGT  ACGAGTGGCA
 901  CTAGTGGGCC  TGGAGGCCTG  GACCCAGCGT  GACCTGGTGG  AGATCAGCCC
 951  AAAACCCAGT  GTCACCCTCG  AAAACTTCCT  CCACTGGCGC  AGGGCACATT
1001  TGCTGCCTCG  ATTGCCCCAT  GACAGTGCCC  AGCTGGTGAC  TGGTACTTCA
1051  TTCTCTGGGC  CTACGGTGGG  CATGGCCATT  CAGAACTCCA  TCTGTTCTCC
1101  TGACTTCTCA  GGAGGTGTGA  ACATGGACCA  CTCCACCAGC  ATCCTGGGAG
1151  TCGCCTCCTC  CATAGCCCAT  GAGTTGGGCC  ACAGCCTGGG  CCTGGACCAT
1201  GATTTGCCTG  GGAATAGCTG  CCCCTGTCCA  GGTCCAGCCC  CAGCCAAGAC
1251  CTGCATCATG  GAGGCCCTCA  CAGACTTCCT  ACCAGGCCTG  AACTTCAGCA
1301  ACTGCAGCCG  ACGGGCCCTG  GAGAAAGCCC  TCCTGGATGG  AATGGGCAGC
1351  TGCCTCTTCG  AACGGCTGCC  TAGCCTACCC  CCTATGGCTG  CTTTCTGCGG
1401  AAATATGTTT  GTGGAGCCGG  GCGAGCAGTG  TGACTGTGGC  TTCCTGGATG
1451  ACTGCGTCGA  TCCCTGCTGT  GATTCTTTGA  CCTGCCAGCT  GAGGCCAGGT
```

FIG. 1A

```
1501 GCACAGTGTG CATCTGACGG ACCTGTTGT CAAAATTGCC AGCTGCGCCC
1551 GTCTGGCTGG CAGTGTCGTC CTACCAGAGG GGATTGTGAC TTGCCTGAAT
1601 TCTGCCAGG  AGACAGCTCC CAGTGTCCCC CTGATGTCAG CCTAGGGAT
1651 GGGCAGCCCT GCGCTGGCGG GCAAGCTGTG TGCATGCACG GGCGTTGTGC
1701 CTCCTATGCC CAGCAGTGCC AGTCACTTTG GGGACCTGGA GCCCAGCCCG
1751 CTGCGCCACT TTGCCTCCAG ACAGCTAATA CTCGGGGAAA TGCTTTTGGG
1801 AGCTGTGGGC GCAACCCCAG TGGCAGTTAT GTGTCCTGCA CCCCTAGAGA
1851 TGCCATTTGT GGGCAGCTCC AGTGCCAGAC AGGTAGGACC CAGCCTCTGC
1901 TGGGCTCCAT CCGGGATCTA CTCTGGGAGA CAATAGATGT GAATGGGACT
1951 GAGCTGAACT GCAGCTGGGT GCACCTGGAC CTGGGCAGTG ATGTGGCCCA
2001 GCCCCTCCTG ACTCTGCCTG GCACAGAGCCTG TGGCCCTGGC CTGGTGTGTA
2051 TAGACCATCG ATGCCAGCGT GTGGATCTCC TGGGGCACA GGAATGTCGA
2101 AGCAAATGCC ATGGACATGG GGTCTGTGAC AGCAACAGGC ACTGCTACTG
2151 TGAGGAGGGC TGGGCACCCC CTGACTGCAC CTCCTCAGCC CACTCAGCTC AAAGCAACCA
2201 GCTCCCTGAC CACAGGGCTG CTCCTCAGCC TCCTGGTCTT ATTGGTCCTG
2251 GTGATGCTTG GCAGCTGGTA CTGTACCCGT GCCCGCCTGC ACCAGCGACT
2301 CTGCCAGCTC AAGGGACCCA CCTGCCAGTA CAGGGCAGCC CAATCTGGTC
2351 CCTCTGAACG GCCAGGACCT CGGCAGAGGG CCCTGCTGGC ACGAGGCACT
2401 AAGGCTAGTG CTCTCAGCTT CCCGGCCCCC CCTTCCAGGC CGCTGCCGCC
2451 TGACCCTGTG TCCAAGAGAC TCCAGTCTCA GGGGCCAGCC AAGCCCCAC
2501 CCCCAAGGAA GCCACTGCCT GCCGACCCCC AGGGCCGGTG CCCATGGGT
2551 GACCTGCCCG GCCCAGGGGC TGGAATCCCG CCCCTAGTGG TACCCTCCAG
2601 ACCAGCGCCA CCGCCTCCGA CAGTGTCCTC GTCTACCTC TGACCTCTCC
2651 GGAGGTTCCG CTGCCTCCAA GCCGGACTTA GGGCTTCAAG AGGCGGGCGT
2701 GCCCTCTGGA GTCCCCTACC ATGACTGAAG GCGCCAGAGA CTGGCGGTGT
2751 CTTAAGACTC CGGGCACCGC CACGCGCTGT CAAGCAACAC TCTGCGACC
2801 TGCCGGCGTA GTTGCAGCGG GGGCTTGGGG AGGGGCTGGG GGTTGGACGG
2851 GATTGAGGAA GGTCCGGCACA GCCTGTCTCT GCTCAGTTGC AATAAACGTG
2901 ACATCTTGGA AAAAAAAAA AAAAAAAAAA AAAAAAAAAA AAAAAAAA
2951 AAAAAAAAA  AAAAAAA
                                                        (SEQ ID NO: 1)
```

FIG. 1B

FEATURES:
5'UTR: 1 - 75
Start Codon: 76
Stop Codon: 2641
3'UTR: 2644

Homologous proteins:

Top 10 BLAST Hits:

Sequences producing significant alignments:

| | Score (bits) | E Value |
|---|---|---|
| CRA\|3350010986403223 /altid=gi\|7451525 /def=pir\|\|G02390 disinteg... | 1714 | 0.0 |
| CRA\|3350010986339998 /altid=gi\|11497002 /def=ref\|NP_003806.2\| a ... | 1698 | 0.0 |
| CRA\|1000682348196 /altid=gi\|9945328 /def=ref\|NP_064704.1\| a dis... | 1377 | 0.0 |
| CRA\|1800005154484 /altid=gi\|6752962 /def=ref\|NP_033744.1\| a di... | 1351 | 0.0 |
| CRA\|1000737073449 /altid=gi\|6682839 /def=dbj\|BAA88903.1\| (AB022... | 1319 | 0.0 |
| CRA\|1570001403283266 /altid=gi\|12720142 /def=ref\|XP_010635.1\| a ... | 970 | 0.0 |
| CRA\|1800005119563 /altid=gi\|4501905 /def=ref\|NP_003465.1\| a di... | 539 | e-152 |
| CRA\|9800004362903234 /altid=gi\|13027660 /def=gb\|AAC08702.2\| (AF02... | 539 | e-152 |
| CRA\|1800005009258 /altid=gi\|6680640 /def=ref\|NP_031426.1\| a di... | 538 | e-151 |
| CRA\|9800004360687 /altid=gi\|12802370 /def=gb\|AAK07852.1\|AF3113... | 517 | e-145 |

EST:

Sequences producing significant alignments:

| | Score (bits) | E Value |
|---|---|---|
| gi\|12777372 /dataset=dbest /taxon=960... | 1750 | 0.0 |
| gi\|10205626 /dataset=dbest /taxon=96... | 1364 | 0.0 |

FIG.1C

| | | |
|---|---|---|
| gi\|10746030 | /dataset=dbest /taxon=96... | 1352 0.0 |
| gi\|12758166 | /dataset=dbest /taxon=960... | 1334 0.0 |
| gi\|13130161 | /dataset=dbest /taxon=960... | 1306 0.0 |
| gi\|11003698 | /dataset=dbest /taxon=96... | 1298 0.0 |
| gi\|12763891 | /dataset=dbest /taxon=960... | 1281 0.0 |
| gi\|9124688 | /dataset=dbest /taxon=9606... | 1211 0.0 |

EXPRESSION INFORMATION FOR MODULATORY USE:

gi\|12777372 placenta
gi\|10205626 lung
gi\|10746030 ovary
gi\|12758166 colon
gi\|13130161 kidney
gi\|11003698 thyroid gland
gi\|12763891 prostate
gi\|9124688 eye Tissue expression:
leucocyte

FIG.1D

```
  1 MRLALLWALG LLGAGSPLPS WPLPNIALLS IPSVLSWGVL GPAGGTEEQQ
 51 AESEKAPREP LEPQVLQDDL PISLKKVLQT SLPEPLRIKL ELDGDSHILE
101 LLQNRELVPG RPTLVWYQPD GTRVVSEGHT LENCCYQGRV RGYAGSWVSI
151 CTCSGLRGLV VLTPERSYTL EQGPGDLQGP PIISRIQDLH LPGHTCALSW
201 RESVHTQTPP EHPLGQRHIR RRDVVTETK TVELVIVADH SEAQKYRDFQ
251 HLLNRTLEVA LLLDTFFRPL NVRVALVGLE AWTQRDLVEI SPNPAVTLEN
301 FLHWRRAHLL PRLPHDSAQL VTGTSFSGPT VGMAIQNSIC SPDFSGGVNM
351 DHSTSILGVA SSIAHELGHS LGLDHDLPGN SCPCPGPAPA KTCIMEASTD
401 FLPGLNFSNC SRRALEKALL DGMGSCLFER LPSLPPMAAF CGNMFVEPGE
451 QCDCGFLDDC VDPCCDSLTC QLRPGAQCAS DGPCCQNCQL RPSGWQCRPT
501 RGDCDLPEFC PGDSSQCPPD VSLGDGEPCA GGQAVCMHGR CASYAQQCQS
551 LWGPGAQPAA PLCLQTANTR GNAFGSCGRN PSGSYVSCTP RDAICGQLQC
601 QTGRTQPLLG SIRDLLWETI DVNGTELNCS WVHLDLGSDV AQPLLTLPGT
651 ACGPGLVCID HRCQRVDLLG AQECRSKCHG HGVCDSNRHC YCEEGWAPPD
701 CTTQLKATSS LTTGLLLSLL VLLVLMLGA SYWYRARLHQ RLCQLKGPTC
751 QYRAAQSGPS ERPGPPQRAL LARGTKASAL SFPAPPSRPL PPDPVSKRLQ
801 SGPAKPPPP RKPLPADPQG RCPSGDLPGP GAGIPPLVVP SRPAPPPPTV
851 SSLYL
    (SEQ ID NO:2)
```

FEATURES:
Functional domains and key regions:
[1] PDOC00001 PS00001 ASN_GLYCOSYLATION
N-glycosylation site Number of matches: 5
  1   254-257  NRTL
  2   406-409  NFSN

FIG. 2A

```
     3   409-412 NCSR
     4   623-626 NGTE
     5   628-631 NCSW
-------------------------------------------
[2] PDOC00005 PS00005 PKC_PHOSPHO_SITE
Protein kinase C phosphorylation site Number of matches: 11
     1    53-55  SEK
     2    73-75  SLK
     3   199-201 SWR
     4   283-285 TQR
     5   411-413 SRR
     6   589-591 TPR
     7   602-604 TGR
     8   611-613 SIR
     9   686-688 SNR
    10   760-762 SER
    11   796-798 SKR
-------------------------------------------
[3] PDOC00006 PS00006 CK2_PHOSPHO_SITE
Casein kinase II phosphorylation site Number of matches: 8
     1    81-84  SLPE
     2   199-202 SWRE
     3   208-211 TPPE
     4   283-286 TQRD
```

FIG. 2B

```
5  500-503  TRGD
6  522-525  SLGD
7  589-592  TPRD
8  611-614  SIRD
```

[4] PDOC00008 PS00008 MYRISTYL
N-myristoylation site

Number of matches: 18

```
 1   10-15   GLLGAG
 2  145-150  GSWVSI
 3  323-328  GTSFSG
 4  358-363  GVASSI
 5  404-409  GLNFSN
 6  422-427  GMGSCL
 7  475-480  GAQCAS
 8  532-537  GQAVCM
 9  555-560  GAQPAA
10  571-576  GNAFGS
11  583-588  GSYVSC
12  596-601  GQLQCQ
13  624-629  GTELNC
14  637-642  GSDVAQ
15  670-675  GAQECR
16  682-687  GVCDSN
17  714-719  GLLLSL
18  774-779  GTKASA
```

FIG.2C

[5] PDOC00016 PS00016 RGD
Cell attachment sequence 501-503 RGD

[6] PDOC00021 PS01186 EGF_2
EGF-like domain signature 2

690-701 CYCEEGWAPPDC

[7] PDOC00129 PS00142 ZINC_PROTEASE
Neutral zinc metallopeptidases, zinc-binding region signature 362-371 SIAHELGHSL Membrane spanning structure and domains:

| Helix | Begin | End | Score | Certainty |
|---|---|---|---|---|
| 1 | 25 | 45 | 1.602 | Certain |
| 2 | 144 | 164 | 0.925 | Putative |
| 3 | 317 | 337 | 1.237 | Certain |
| 4 | 430 | 450 | 0.768 | Putative |
| 5 | 547 | 567 | 0.601 | Putative |
| 6 | 640 | 660 | 1.243 | Certain |
| 7 | 711 | 731 | 2.394 | Certain |

FIG.2D

BLAST Alignment to Top Hit:
Alignment to top blast hit:

>CRA|3350010986403223 /altid=gi|7451525 /def=pir||G02390 disintegrin
and metalloproteinase MDC15 (EC 3.4.24.-) - human /org=human /taxon=9606 /dataset=nraa /length=814
Length = 814

Score = 1714 bits (4390), Expect = 0.0
Identities = 812/855 (94%), Positives = 812/855 (94%)
Frame = +1

```
Query: 76   MRLALLWALGLLGAGSPLPSWPLPNIALLSIPSVLSWGVLGPAGGTEEQQAESEKAPREP  255
            MRLALLWALGLLGAGSPLPSWPLPNI                 GGTEEQQAESEKAPREP
Sbjct: 1    MRLALLWALGLLGAGSPLPSWPLPNI-----------------GGTEEQQAESEKAPREP  43

Query: 256  LEPQVLQDDLPISLKKVLQTSLPEPLRIKLELDGDSHILELLQNRELVPGRPTLVWYQPD  435
            LEPQVLQDDLPISLKKVLQTSLPEPLRIKLELDGDSHILELLQNRELVPGRPTLVWYQPD
Sbjct: 44   LEPQVLQDDLPISLKKVLQTSLPEPLRIKLELDGDSHILELLQNRELVPGRPTLVWYQPD  103

Query: 436  GTRVVSEGHTLENCCYQGRVRGYAGSWVSICTCSGLRGLVVLTPERSYTLEQGPGDLQGP  615
            GTRVVSEGHTLENCCYQGRVRGYAGSWVSICTCSGLRGLVVLTPERSYTLEQGPGDLQGP
Sbjct: 104  GTRVVSEGHTLENCCYQGRVRGYAGSWVSICTCSGLRGLVVLTPERSYTLEQGPGDLQGP  163

Query: 616  PIISRIQDLHLPGHTCALSWRESVHTQTPPEHPLGQRHIRRRRDVVTETKTVELVIVADH  795
            PIISRIQDLHLPGHTCALSWRESVHTQTPPEHPLGQRHIRRRRDVVTETKTVELVIVADH
Sbjct: 164  PIISRIQDLHLPGHTCALSWRESVHTQTPPEHPLGQRHIRRRRDVVTETKTVELVIVADH  223
```

FIG. 2E

```
Query:  796  SEAQKYRDFQHLLNRTLEVALLLDTFFRPLNVRVALVGLEAWTQRDLVEISPNPAVTLEN   975
Sbjct:  224  SEAQKYRDFQHLLNRTLEVALLLDTFFRPLNVRVALVGLEAWTQRDLVEISPNPAVTLEN   283

Query:  976  FLHWRRAHLLPRLPHDSAQLVTGTSFSGPTVGMAIQNSICSPDFSGGVNMDHSTSILGVA  1155
Sbjct:  284  FLHWRRAHLLPRLPHDSAQLVTGTSFSGPTVGMAIQNSICSPDFSGGVNMDHSTSILGVA   343

Query: 1156  SSIAHELGHSLGLDHDLPGNSCPCPGPAPAKTCIMEASTDFLPGLNFSNCSRRALEKALL  1335
Sbjct:  344  SSIAHELGHSLGLDHDLPGNSCPCPGPAPAKTCIMEASTDFLPGLNFSNCSRRALEKALL   403

Query: 1336  DGMGSCLFERLPSLPPMAAFCGNMFVEPGEQCDCGFLDDCVDPCCDSLTCQLRPGAQCAS  1515
Sbjct:  404  DGMGSCLFERLPSLPPMAAFCGNMFVEPGEQCDCGFLDDCVDPCCDSLTCQLRPGAQCAS   463

Query: 1516  DGPCCQNCQLRPSGWQCRPTRGDCDLPEFCPGDSSQCPPDVSLGDGEPCAGGQAVCMHGR  1695
Sbjct:  464  DGPCCQNCQLRPSGWQCRPTRGDCDLPEFCPGDSSQCPPDVSLGDGEPCAGGQAVCMHGR   523

Query: 1696  CASYAQQCQSLWGPGAQPAAPLCLQTANTRGNAFGSCGRNPSGSYVSCTPRDAICGQLQC  1875
Sbjct:  524  CASYAQQCQSLWGPGAQPAAPLCLQTANTRGNAFGSCGRNPSGSYVSCTPRDAICGQLQC   583

Query: 1876  QTGRTQPLLGSIRDLLWETIDVNGTELNCSWHLDLGSDVAQPLLTLPGTACGPGLVCID  2055
Sbjct:  584  QTGRTQPLLGSIRDLLWETIDVNGTELNCSWHLDLGSDVAQPLLTLPGTACGPGLVCID   643
```

FIG.2F

```
Query:  2056  HRCQRVDLLGAQECRSKCHGHGVCDSNRHCYCEEGWAPPDCTTQLKATSSLTTGLLLSLL  2235
              HRCQRVDLLGAQECRSKCHGHGVCDSNRHCYCEEGWAPPDCTTQLKATSSLTTGLLLSLL
Sbjct:   644  HRCQRVDLLGAQECRSKCHGHGVCDSNRHCYCEEGWAPPDCTTQLKATSSLTTGLLLSLL   703

Query:  2236  VLLVLVMLGASYWYRARLHQRLCQLKGPTCQYRAAQSGPSERPGPPQRALLARGTKASAL  2415
              VLLVLVMLGASYWYRARL  QRLCQLKGPTCQYRAAQSGPSERPGPPQRALLARGTK
Sbjct:   704  VLLVLVMLGASYWYRARLXQRLCQLKGPTCQYRAAQSGPSERPGPPQRALLARGTK----   759

Query:  2416  SFPAPPSRPLPPDPVSKRLQSQGPAKPPPPRKPLPADPQGRCPSGDLPGPGAGIPPLVVP  2595
                                  SQGPAKPPPPRKPLPADPQGRCPSGDLPGPG GIPPLVVP
Sbjct:   760  --------------------SQGPAKPPPPRKPLPADPQGRCPSGDLPGPGPGIPPLVVP   799

Query:  2596  SRPAPPPTVSSLYL  2640
              SRPAPPPTVSSLYL
Sbjct:   800  SRPAPPPTVSSLYL  814  (SEQ ID NO:4)

Hmmer search results (Pfam):
Scores for sequence family classification (score includes all domains):
Model     Description                                       Score   E-value  N
-------   -----------                                       -----   -------  -
PF01421   Reprolysin (M12B) family zinc metalloproteas      259.3   5.3e-74  1
PF01562   Reprolysin family propeptide                      128.4   2.1e-35  1
PF00200   Disintegrin                                        70.0   3.4e-22  1
CE00385   E00385 platelet_aggregation_activation_inhib       26.5   5.4e-06  1
PF00035   Double-stranded RNA binding motif                   7.2   1.2      1
CE00423   E00423 stromelysin_1                                4.5   0.99     1
PF01400   Astacin (Peptidase family M12A)                     2.6   7.8      1
```

FIG. 2G

Parsed for domains:

| Model | Domain | seq-f | seq-t | hmm-f | hmm-t | | score | E-value |
|---|---|---|---|---|---|---|---|---|
| PF01562 | 1/1 | 100 | 217 | 1 | 119 | [] | 128.4 | 2.1e-35 |
| PF01400 | 1/1 | 363 | 373 | 91 | 101 | .. | 2.6 | 7.8 |
| CE00423 | 1/1 | 364 | 375 | 222 | 233 | .. | 4.5 | 0.99 |
| PF01421 | 1/1 | 230 | 428 | 1 | 200 | [. | 259.3 | 5.3e-74 |
| CE00385 | 1/1 | 447 | 518 | 1 | 67 | [. | 26.5 | 5.4e-06 |
| PF00200 | 1/1 | 447 | 523 | 1 | 76 | [] | 70.0 | 3.4e-22 |
| PF00035 | 1/1 | 734 | 766 | 1 | 37 | [. | 7.2 | 1.2 |

FIG.2H

```
   1 TTGGGTGACC CTGGGCAGTG ATCACATCTC CAAGCATCAG TTTTCTCACC
  51 TGAAAAAAAG GAGATGATAA TAACACTATC TGCCTTACAT GACAATTGAA
 101 TTGAATTTTT TTTTTTTTTT TGAGACTAAG TCTCACTCTG TCGCCCAGGC
 151 TGGAGTGCAG TGGCGTGATC TTGGCTCACT GCAACCTCCA CCTCCCCAGT
 201 TCAAGCGATT CTCGTGCCTC AGCTTCCCGA GTAGCTGGGA TTACAGGCAC
 251 ACACTACCAC GCCCGGCTAA TTTAGAATTG AAATAATTTA TGTACAGTAT
 301 CTTAGTACAG GACCTGACAT TATAAACAAT GAGTGGCAGC CATTCTTATT
 351 TAATCAGTCC TAACAAAGTT CATAAAAGTG AGACTGTGTT TGCTTAGCTT
 401 TTTCCCTAGG GCCTGGATAC CCCCAGCCCC CATGACACAC AATAGGGGCC
 451 AAATGAATGT GTTGTGAAAA AATGAAAAAC AAAAAACAAA AAAGAACATG
 501 CTGGGATTCC TTGACAGGGT CGTGAAGCAA ACTGAATGTG AATGCACAGA
 551 TGGAAATGTG CCAGACAGTC ATTCCAAGCA GAATGTGCAA AGACTCAGTC
 601 CACAGGGAAT GCGAAGTGCC AGGGCTAGTC TCAGGAGAAA CTGGCTCAGA
 651 AGAGACAGCT CTCAGGGAGG GCTAAAGTAG GAAAGAGGCT AGAAAGGGAC
 701 CAGGTGAGGG AAGGCTCTGA AGGCCAAGCC CAAGAGTTCT GCCTGTCTGG
 751 CAGGCAGCAG GGCCTCTGGA GTTTCTTGGG CAAAGAGTGG CTGCTTCCTG
 801 GGTAAGGTGG CCTGTGGAAA ATCCCTGACA ACTGTGTAGA GACATGTCGT
 851 GAGGGATGGC AGGGAGCATA GTGAACTAGG TTTGTGGTTT GGAATCAGGG
 901 CCCCTGGGGT CCAGCCAAGT TGGATTGTTT ACTATCTGTG TGACTTTGAG
 951 AGTCACTTCA CCTTTCTCAA CTGTAAAGTG GGGATAGCAA CAGTGATAGT
1001 CGATCTGGCC TGCTCACTTC TCAGCCTCAC TGTGAGAACC AAATAAGATG
1051 ATTTACAGGA AAGTGCAAAT GAGAGTTGTG GCTGATATCC GCTTGGAGAG
1101 AGCCTGGAGG GTGCATCCTC CCATTCTCCA TCACAGAGTT GGGGAGGGAG
1151 GCACCCTCGC CCTCCAGGGG TTTCCTTTGT CCAACCCAGC CTCCTCCAAC
1201 ACGCGGGAAT TGTCAGGCCT GGCGACTTCA GACAGGAAAC GCTGTCCAGT
1251 TCCCCTTCTT TCCCGCCTCG CTCCCGGGCT GGCGCTAACG CCCACCTCCC
1301 AACAGCGCCA CCCGCTGGCG GATATCCTGC ACCGCGGCTG CCCGCTCCTG
1351 CGCCGCTGGC TGTGCCGGCG CTGCGTGGTG TGCCAGGCAC CCGAGACGCC
1401 CGAGTCCTAC GTGTGCCGGA CGCTGGACTG CGAGGCCGTG TACTGCTGGT
1451 CGTGCTGGGA CGACATGCGG CAGCGGTGCC CGGTCTGCAC GCCCCGCGAA
1501 GAGCTCTCTT CCTCCGCCTT TAGTGACAGC AACGACGACA CTGCCTACGC
1551 GGGGTGAAGA GGCGTCCTGC TCGCTCTTCC GCACCGTCCT TCCCGGTTAA
1601 TAAAATGCCC TGTACGCTTC ACGTGGGTCG GGGACTGGGG TGAGCCGCGC
1651 ACTGCCTCGC CTGCAGTCGG GAAAGCCTGC CCGCCCGACC TCTCCGAGCC
1701 AGGCCGCGCA CAGGAGGCAG GGAGGCCGCG AAGCTACTAG GGAGGGGTCC
1751 GGACCTGGCG CCGGGTGAAG GCGCGCCGCC CAAGCCGGTC GGACCGGGCA
1801 CCGGCTCCCA CTCCGCACAG TTGCGGGGAA GCGGTAGCGC TGAGCAGCGC
1851 GGGCGTAGTG GGCGGTGTCC CCGCTCCCGA GGCACCCGGC GCGCAGCGGG
1901 GCGGGCTTTG CCGGGGGCGG AGCTTGGCTT GGGGCCGGGT GGGAGGGGGC
1951 GGGCCGGGGC GGGGCCTGGT GGCCGCGCGG CGCTGCTGGG TTCTCCGAGG
2001 CGACCTGGCC GCCGGCCGCT CCTCCGCGCG CTGTTCCGCA CTTGCTGCCC
2051 TCGCCCGGCC CGGAGCGCCG CTGCCATGCG GCTGGCGCTG CTCTGGGCCC
2101 TGGGGCTCCT GGGCGCGGGC AGCCCTCTGC CTTCCTGGCC GCTCCCAAAT
2151 ATAGGTGAGT CCTCCGCCTG GAGTGGGTCG GGGGCGGAC TGGGAGGGAG
2201 GTGCAGGAAA GTCGGAAGGC ATTAGGGTAA TGGGGCCGGA CGGAGACCCT
```

FIG.3A

```
2251 GGGAGAGCCC AGCCAGAGCG CGGCCCGCCC TGGTCCGCTG TCCTGGGCCT
2301 AGGGCCCGGT GACTTGGCGA TGGGGTGAAA AGAGAAGGAG GGGGGATGCC
2351 GGCGCCCCCT GCCTCCTGCC TGGTCATCCT CTGCGCGGTC CCTGCGGACA
2401 CTTTCAGGCT CAGGTACCAG GTACCGAGGG GCCTGTCCAG CGCCACTTCA
2451 AGATCGTGAT GAGAGGGTCG CTGCTCCCCA GGACTGGCAT CTTCGCTGCT
2501 CTGGGGCCTA GCTAACCGTT CCACCCGGTG CCAGGGCGCT GAGCGGGCAT
2551 GGCTTGTAGG GTTTAGTGAA GAGGATTCTC TCTAGCCTCT ATTCCAGGCC
2601 TGGGGCCGCC AGGCACTCCT CACCCTGGTG CTGTTGCCAC CAGTGCCTGG
2651 CCGAGCGGGA GGGGCCCGAG ATGAGCCAGG AGAAGGGAGA ATTGGCCAGG
2701 AAAGAGGCTG GGACACCAAC TCCTCCTTGG AACTTTCACT TCCCGCTGCT
2751 GTCTTGGGCC GGGACCGAGA GGGCAGGCGC GGGTGGAGTG TCCGGAGGAG
2801 AGAGGGCCAT TGTGTGTTGG GGGGGTGGGG GGTGCTCGAG GAGGAAGCAG
2851 AGGCTGTAGG CAGCGGGTGT GCCTGACTGG GCATGAGGGT GTTTAGGGAG
2901 GTGGGGGTGT TTGCACTGCT CACCCAGAAA TGGGCGTTCC TGGCATCTCC
2951 GATGTGAGCG AAGGGGAGGG TGAGCGGGCA CCCGGCCACA AGGCTTAGCT
3001 CAGTCTCGAG AGGGGGCGTT CCTGAAGTGG GGGGAGAGTG ATTGGGAGGG
3051 AGTGGGAACC GCGGAGGGTC CTGTGAGAAC CTGGGATTGG CCGGAAGGGG
3101 ACAAGGAGGG CCACAGGCTG CGCAAGCCGA AAGTCTTTCT TGGGGACTTG
3151 TGAATGGGTT GGTGGGTGGA AAGCCATAAA TTAGAGAGAC ACCCTCTCCT
3201 TCCAGTATTC TTCTTTAAGT CTCAGCATGC AATGTGGAAG CCCCTCAGGT
3251 ACCTAAGGGT CTTGATGGGC TGGGAGCTGG TGGATCTGAG GCACCTGTC
3301 ACCCCAGCC CTGCTGTCGA TTCCCTCAGT ACTGTCTTGG GGTGTCCTGG
3351 GACCTGCAGG TGGCACTGAG GAGCAGCAGG CAGAGTCAGA GAAGGCCCCG
3401 AGGGAGCCCT TGGAGCCCCA GGTCCTTCAG GACGATCTCC CAATTAGCCT
3451 CAAAAAGGTG CTTCAGGTGA GCTCTCACTC CCCTCTAATA AATAAACGAA
3501 TCCACACACG CCCCGGTATA GCCAGGTGTC TCAAAGCCAA AGCTTGGCTG
3551 AGGAGCTGGT GGGTAGAGCT CACTGTAGTG GGTCTATCCC AGGCCCAGCT
3601 GCCTCTCCCA CCACACCCCA GCACCTGGCT TCACTTATCT CCCTCTCCCT
3651 CTGCACACAC GTGTATCTGT CTGCCTCAGC CCCACCCAAC CCATCCATCT
3701 CCACTGGGGA AATTGTGAAG CCAAACTTGC TTTCTTCATC TCATGTTGTC
3751 GGTTTTCTCA GTGGGGGGAT TTGGAAAGAG TCAGGACCTT ACCAAACCCC
3801 CCCCCCCCAC CCCATTCTAA AGCTGAGTCA GAGGAAGGGC TGGGGCTTGT
3851 GCTGGGTCCT ACACGGTGCT TCCTCTCTGG GCAGGAAGCC GAGAAGGGGT
3901 GGCTCAGATA CCTTCCTTGA CCTCCGCACA CAACCCCCCA GAACAATGCT
3951 CCAGGCCAGG CAGGGTTTCC TGGCCCCTCC CCTGGGATCC CCCCACCAGT
4001 GATCTAATTG CTGGTGCTCT TCTGTGGGCC TGAGGTTTTC TGGTTAGAGA
4051 GGCTGGGAGT TGTGGACAGG TCTAGGGAGG TGACCTGCCC TCTGGTGCCC
4101 ACAGACCAGT CTGCCTGAGC CCCTGAGGAT CAAGTTGGAG CTGGACGGTG
4151 ACAGTCATAT CCTGGAGCTG CTACAGAATA GGTAATAGTG ATGGTGGCAA
4201 TAACAGTGAC CACATGGCCA ACAACTTGTA TAGCATTTAT TATGTGCCAG
4251 GTACTAAGTG CTTGTGCTCA TTTAATCCTC ATAACAGCCC TATAAGGGAT
4301 ATACTATCAT GTATTATTGT CCTCACTTTA TACATGAGGA AGTCAAGGCA
4351 CAGAGAGATT AAATAACTTG CCCCAGGTCA CACAGCTAGT ATGTGGTGAA
4401 AACCAGATTG GAATTCAAAT AAACTAACAG AGTCAGTGGC CCAACCAGTA
4451 TACTTTGCTG CCCCGGGGTC AGGAGTGGAA AAGTTGGCTG CGGGGGTTGC
```

FIG.3B

```
4501 CTGGTCCCCA GCCCCACAAC CACCTTCAAG CCTCTGCTTG TCAATGCACC
4551 GACCCTGGGA AGTGGCTTTA GCACTGCCTT CTTTTTCTTC ACTTCACAGG
4601 GGAGTTGGTC CCATGTCCGC CCCGACCCTT GGGGTCCGGC TNTCCCCTCT
4651 CCCCCCTTCG GCGCCGCCCC TTCCCTTTTC TTTCTTCCCC TCCGCTTTCG
4701 TCCTTTTGCC TCCCCCGTGC CGTTGCGCGT TCCTTCTTCC CCGTTCCCTC
4751 TCCCCTCTTT TGTTCCCTCC CGTTCTTTTC TCCCCCGCGT TCTTTCCTCC
4801 TCCTTTTCGG TCCGCCCTCG CCTTCCTCCC TTCCCCTTCT GCCCTTCGCC
4851 NTTTCTCCCT CTCGTTCTTC CTCGGTGTCG CGTCGTCCCG GCTCGGCCTT
4901 TCCCCGCTTC CTCCCGCTCG CCGTTTTTTT CCCCCCGCTG TCTTCCCGTG
4951 TTCCCCTTCG CTTCTCCTCT TCCCTTTCGT TCGGTCGTTT TCTCGTTCCA
5001 TTCCCGCCTC CCCGTTTCCG TTCCACTCCT TCTTCCTCCT TTCCCGCTCC
5051 CCGTTTCTCC CGACCCCAAC AACAAATAAA NNNNNNNNNN NNNNNNNNNN
5101 NNNNNNNNNN NNNNNNNNNN NNNNNNNNNN NNNNNNNNNN NNNNNNNNNN
5151 NNNNNNNNNN NNNNNNNNNN NNNNNNNNNN NNNNNNNNNN NNNNNNNNNN
5201 NNNNNNNNNN NNNNNNNNNN NNNNNNNNNN NNNNNNNNNN NNNNNNNNNN
5251 NNNNNNNNNN NNNNNNNNNN NNNNNNNNNN NNNNNNNNNN NNNNNNNNNN
5301 NNNNNNNNNN NNNNNNNNNN NNNNNNNNNN NNNNNNNNNN NNNNNNNNNN
5351 NNNNNNNNNN NNNNNNNNNN NNNNNNNNNN NNNNNNNNNN NNNNNNNNNN
5401 NNNNNNNNNN NNNNNNNNNN NNNNNNNNNN NNNNNNNNNN NNNNNNNNNN
5451 NNNNNNNNNN NNNNNNNNNN NNNNNNNNNN NNNNNNNNNN NNNNNTCAGG
5501 AGGCCGAGTG GAAGAATCGC TTGAGCCCAG GTAGGCAGAG GTTTCAGTGG
5551 GCCGAGATCG AGCCACTACA CACCAGCCTG GGTGAAAGAG TGAGACCTCG
5601 TCTCAAAAAA TAAAATAAAA ATAAAATAAA ATAAAATCTA GCTGAGACAG
5651 ATTAGGTGGT TTGCCCGAGG CCCTACAACT AATAAATGGC CTATCCATTT
5701 ATTAGTTGTA TTTGGCTCTT CATCTGTCTT ATGATCCCAT TTGCAGAGAG
5751 CTCTCACTTG GTTATAGATA ATACATAGTT ACCAATGATG AAGCAATATA
5801 AACCCAATTT CCTAATTTGT AAAATGAAGA TAATAAAACT ACTTGCTGCA
5851 TAGAGTTGCT GGGAAGATTA AATAAGTCCA TATAGATGTA AAGTGCTTAA
5901 AACTATGCCA GACCTATGGT AAGTGACAAG AGTTGTTATT GGGATTTTTA
5951 AAATTATTAT TATTATTATT ATTATTATTT GAGACAGAGT CTCGCTCTGT
6001 CTCCCAGGCT GGAGTGCAGT GGCGTGATCT CGGCTCACTG CAAGCTCCGC
6051 CTCCCAGGTT CACGCCATTC TCTTGCCTCA GCCTCCCGAG TAGCTGGGAC
6101 TACAGGCGCC CGCCACTACA CCCGGCTAAT GTTTTGTATT TTTTAGTACA
6151 GACAGGGTTT CACCGTGTTA TCCAGGATGG TCTCGATCTC CTGACCTCAT
6201 GATCCACCCG CCTTGTCCTC CCAAAGTGCT GAGATTACAG GCGTGAGCCA
6251 CCGCACCCAG CTAAATTACT GTTTTTTAAA AATTTGAAAA AAACCACTGA
6301 GTTTGGAGCC AGAAAAGCAG GGGTCTACTC CAACCTTCAT TATCTACTTC
6351 CTGGTCCTCC TTGGCAAGTT CCTGGGCCCT CTGGCCTTCA GTGGCTCATC
6401 TGTAAAATGG GCTCTTCACC CTCCTATTTG ACCCACAGAG TAGGAGTGGC
6451 TGCCTCTTGG TCAGCCCGGC ACAGCTGCTG GCTGCGAGCG GCAGGTTTGC
6501 CTGATAATTC TTCTTGTCCA TAGTAGAGGC GGGATGTGGT AACAGAGACC
6551 AAGACTGTGG AGTTGGTGAT TGTGGCTGAT CACTCGGAGG TGAGCCTGCT
6601 GGCCCCTGCA CATCCTCCTC CCCCTGCACT GCCCTGCCGC CTTTCATGTC
6651 ACCTCTCTTG GCCTACAGGC CCAGAAATAC CGGGACTTCC AGCACCTGCT
6701 AAACCGCACA CTGGAAGTGG CCCTCTTGCT GGACACAGTG AGTGCTGGAC
```

FIG.3C

```
6751 AGGGCAACCC CCACCCCAGG CCCCTGACCA TGGCAACCCC TCTTCTGAGC
6801 CCCAGCTGTC TTTCAGTTCT TCCGGCCCCT GAATGTACGA GTGGCACTAG
6851 TGGGCCTGGA GGCCTGGACC CAGCGTGACC TGGTGGAGAT CAGCCCAAAC
6901 CCAGCTGTCA CCCTCGAAAA CTTCCTCCAC TGGCGCAGGG CACATTTGCT
6951 GCCTCGATTG CCCCATGACA GTGCCCAGCT GGTGACGTAA GGGCCCCAGA
7001 CTCAGCCAGA GAGGCCAGTC CTGTCCTGGC CAAATTCACA CCCCTTCAGC
7051 ACCCTACCTC AGCCCTGAA GCTCTGACCA CCGTGGCTTC TGGCCCTGAA
7101 CTTTAGCCTC TCTGTCCCAC AGTGGTACTT CATTCTCTGG GCCTACGGTG
7151 GGCATGGCCA TTCAGAACTC CATCTGTTCT CCTGACTTCT CAGGAGGTGT
7201 GAACATGGTG AGTTATTTCC AGGTCTCCTC CTCATTCCCA ATTCAGTTCC
7251 TCCCAAGTGT GGTGGCATTT ATGCACTGAA ACCCCCTAT AAAGTTGCCC
7301 AACCCCAAAG CTACAGGTAT AGAGGGTGGA GGTACGTGAT GTGGCCTTTG
7351 CTATCAGGGA GCCCTCGCTT ATGGCCAGCT AGTCACAGTG TACACAGTCA
7401 TCCCCTGTGC AGTCTTCCCA TTTCTTAGAG GAGGGTAGGA GGCAGCTAAG
7451 GCCCAAAGAA CAGAGGTGAT CTCCCTCCAG TGAGGGAGGG GGACAGAGCT
7501 GAGCTAGAAC CCAAGTTTCT GCCATCCAGG CCTGGGTTCT CCTACTTTAG
7551 AAGCAATTCA GGAGGGAAGC AGTGCCTGCT GAGTGCCCAC GAGGTCAGAC
7601 GTGGAGGGAA CAGGAGCAGA GAGGGTGGTC TGGGCATTGT GGTGGAGGCA
7651 GGCTGGGACT GGACCTACAG TACCCCTCCC CAATGACAGG ACCACTCCAC
7701 CAGCATCCTG GGAGTCGCCT CCTCCATAGC CCATGAGTTG GGCCACAGCC
7751 TGGGCCTGGA CCATGATTTG CCTGGGAATA GCTGCCCCTG TCCAGGTCCA
7801 GCCCCAGCCA AGACCTGCAT CATGGAGGCC TCCACAGAGT AAGTAGCTGC
7851 AGGATGGAGA GAGGGTGTGG GGCAGGGGGC AGGGANNNNN NNNNNNNNNN
7901 NNNNNNNNNN TGTTAGAGTT ACCTTCCTTG CCACCCTCCC CAGCTTCCTA
7951 CCAGGCCTGA ACTTCAGCAA CTGCAGCCGA CGGGCCCTGG AGAAAGCCCT
8001 CCTGGATGGA ATGGGCAGCT GCCTCTTCGA ACGGCTGCCT AGCCTACCCC
8051 CTATGGCTGC TTTCTGCGGA AATATGTTTG TGGAGCCGGG CGAGCAGTGT
8101 GACTGTGGCT TCCTGGATGT GAGCCCCTTT CCCAAAGCCT CGCCCCACTC
8151 ACTTCTGTAC CCTCACCCTG GCTCATTAGC CCTATCCCAG CCTCCTGAGC
8201 TCTTGGGTTC TGAAGGGACT TTCCACCCCT CTCCTACTTG CCCTGTCTGT
8251 GGGGACAGCA CATGGGTTGT TGGGCTCTAG CCCTCGCTTG CTGTGTAGCT
8301 TCTGGTCTTG GCCTGTGGGA GGAGGAGAGA TTGGAGGGAG GCTCACAGGC
8351 CCCACCTGCT CTGATGCCCG GCCCCGTGC TCCTGCCCAC AGGACTGCGT
8401 CGATCCCTGC TGTGATTCTT TGACCTGCCA GCTGAGGCCA GGTGCACAGT
8451 GTGCATCTGA CGGACCCTGT TGTCAAAATT GCCAGGTGGG TAGAGACTAG
8501 ACTGGCCACC CGGAGCTCAC CTGCCGGGGC CAAGGTGGAA AGGGTCATTC
8551 TGACCCCCGG CTGGATTTGC TCAGTGCCCA CACTGATGCT CATCCACCCT
8601 CCACAGCTGC GCCCGTCTGG CTGGCAGTGT CGTCCTACCA GAGGGGATTG
8651 TGACTTGCCT GAATTCTGCC CAGGAGACAG CTCCCAGTGT CCCCCTGATG
8701 TCAGCCTAGG GGATGGCGAG CCCTGCGCTG GCGGGCAAGC TGTGTGCATG
8751 CACGGGCGTT GTGCCTCCTA TGCCCAGCAG TGCCAGTCAC TTTGGGGACC
8801 TGGAGCCCAG CCCGCTGCGC CACTTTGCCT CCAGACCGCT AATACTCGGG
8851 GAAATGCTTT TGGGAGCTGT GGGCGCAACC CCAGTGGCAG TTATGTGTCC
8901 TGCACCCCTA GGTAAGTGAG GAAACCTGGC TCCTCCTTTG GGTTTCTGAG
8951 AGCCTTGGCC CTGCTCCTAC TAACTCTGTG TGCCCTTCCC CCTCNNNNNN
```

FIG.3D

```
 9001 NNNNNNNNNN NNNNNNNNNN NNNNNNNNNN NNNNNNNNNN NNNNTTACGG
 9051 CATTTGTAGT TACTCACACT TTTGCCTTCA NACAGCTAAT ACTCGGGGAA
 9101 ATGCTTTTGG GAGCTGTGGG CGCAACCCCA GTGGCAGTTA TGTGTCCTGC
 9151 ACCCCTAGGT AAGTGAGGAA ACCTGGCTCC TCCTTTGGGT TTCTGAGAGC
 9201 CTTGGCCCTG CTCCTACTAA CTCTGTGTGC CCTTCCCCCT CCCCACAGAG
 9251 ATGCCATTTG TGGGCAGCTC CAGTGCCAGA CAGGTAGGAC CCAGCCTCTG
 9301 CTGGGCTCCA TCCGGGATCT ACTCTGGGAG ACAATAGATG TGAATGGGAC
 9351 TGAGCTGAAC TGCAGCTGGG TGCACCTGGA CCTGGGCAGT GATGTGGCCC
 9401 AGCCCCTCCT GACTCTGCCT GGCACAGCCT GTGGCCCTGG CCTGGTGAGC
 9451 AGCCTGGGTG GGCAAGACCA GGTGTGAGAA GGGACATTTG GACCACAATG
 9501 AACAGAGCCC AGACTTCACC ATTCACCAAT GTCAAAGGCA GGGACTCCAA
 9551 GGGAAGTCAG TTTCTTACTT CAGATGGAGC AAAGTCCTAT CAACTCACTA
 9601 TGCCTTGGTT TCCCCATCTG TAAACGCAGG GTATGGCCTC AACCTTATTG
 9651 GCCTCCCAGT CCCATTAAAG CTTTGTGGGA ATCTGATCCA GGCTCTTCTC
 9701 TCCCTGGGTC AGGTGTGTAT AGACCATCGA TGCCAGCGTG TGGATCTCCT
 9751 GGGGGCACAG GAATGTCGAA GCAAATGCCA TGGACATGGG GTGAGCTGGG
 9801 ATGGGGGAAG TGGAAGGGGA GCAGAGAGCC TCTAGAGAGG AAAAGGATAC
 9851 TGGGCTTTGG AAATAGACAT ATCTGGGTTT TAATCCTTGC TCTACTACTT
 9901 CCCAGTTGTG TGACCTCGGG CAGGTTACTA ACTTTGCTGA GCTCAGTTTC
 9951 CCCACCTATC AAATGGCTAT AATAATAGTA TCCCCATCCA GGGTACATGA
10001 GATGTGTATG CAAGCAAGTA GCACAGTGGG TAACTAATAG TGCTTTTAAA
10051 AANNNNNNNN NNNNNNNNNN NNNNNNNNNN NNNNNNNNNN NNNNNNNNNN
10101 NNNNNNNNNN NNNNNNNNNN NNNNNNNNNN NNNNNNNNNN NNNNNNNNNN
10151 NNNNNNNNNN NNNNNNNNNN NNNNNNNNNN NNNNNNNNNN NNNNNNNNNN
10201 NNNNNNNNNN NNNNNNNNNN NNNNNNNNNN NNNNNNNNNN NNNNNNNNNN
10251 NNNNNNNNNN NNNNNNNNNN NNNNNNNNNN NNNNNNNNNN NNNNNNNNNN
10301 NNNNNNNNNN NNNNNNNNNN NNNNNNNNNN NNNNNNNNNN NNNNNNNNNN
10351 NNNNNNNNNN NNNNNNNNNN NNNNNNNNNN NNNNNNNNNN NNNNNNNNNN
10401 NNNNNNNNNN NNNNNNNNNN NNNNNNNNNN NNNNNNNNNN NNNNNNNNNN
10451 NNNNNNNNNN NNNNNNNNNN NNNNNNNNNN NNNNNNNNNN NNNNNNNNNN
10501 NNNNNNNNNN NNNNNNNNNN NNNNNNNNNN NNNNNNNNNN NNNNNNNNNN
10551 NNNNNNNNNN NNNNNNNNNN NNNNNNNNNN NNNNNNNNNN NNNNNNNNNN
10601 NNNNNNNNNN NNNNNNNNNN NNNNNNNNNN NNNNNNNNNN NNNNNNNNNN
10651 NNNNNNNNNN NNNNNNNNNN NNNNNNNNNN NNNNNNNNNN NNNNNNNNNN
10701 NNNNNNNNNN NNNNNNNNNN NNNNNNNNNN NNNNNNNNNN NNNNNNNNNN
10751 NNNNNNNNNN NNNNNNNNNN NNNNNNNNNN NNNNNNNNNN NNNNNNNNNN
10801 NNNNNNNNNN NNNNNNNNNN NNNNNNNNNN NNNNNNNNNN NNNNNNNNNN
10851 NNNNNNNNNN NNNNNNNNNN NNNNNNNNNN NNNNNNNNNN NNNNNNNNNN
10901 NNNNNNNNNN NNNNNNNNNN NNNNNNNNNN NNNNNNNNNN NNNNNNNNNN
10951 NNNNNNNNNN NNNNNNNNNN NNNNNNNNNN NNNNNNNNNN NNNNNNNNNN
11001 NNNNNNNNNN NNNNNNNNNN NNNNNNNNNN NNNNNNNNNN NNNNNNNNNN
11051 NNNNNNNNNN NNNNNNNNNN NNNNNNNNNN NNNNNNNNNN NNNNNNNNNN
11101 NNNNNNNNNN NNNNNNNNNN NNNNNNNNNN NNNNNNNNNN NNNNNNNNNN
11151 NNNNNNNNNN NNNNNNNNNN NNNNNNNNNN NNNNNNNNNN NNNNNNNNNN
11201 NNNNNNNNNN NNNNNNNNNN NNNNNNNNNN NNNNNNNNNN NNNNNNNNNN
```

FIG.3E

```
11251 NNNNNNNNNN NNNNNNNNNN NNNNNNNNNN NNNNNNNNNN NNNNNNNNNN
11301 NNNNNNNNNN NNNNNNNNNN NNNNNNNNNN NNNNNNNNNN NNNNNNNNNN
11351 NNNNNNNNNN NNNNNNNNNN NNNNNNNNNN NNNNNNNNNN NNNNNNNNNN
11401 NNNNNNNNNN NNNNNNNNNN NNNNNNNNNN NNNNNNNNNN NNNNNNNNNN
11451 NNNNNNNNNN NNNNNNNNNN NNNNNNNNNN NNNNNNNNNN NNNNNNNNNN
11501 NNNNNNNNNN NNNNNNNNNN NNNNNNNNNN NNNNNNNNNN NNNNNNNNNN
11551 NNNNNNNNNN NNNNNNNNNN NNNNNNNNNN NNNNNNNNNN NNNNNNNNNN
11601 NNNNNNNNNN NNNNNNNNNN NNNNNNNNNN NNNNNNNNNN NNNNNNNNNN
11651 NNNNNNNNNN NNNNNNNNNN NNNNNNNNNN NNNNNNNNNN NNNNNNNNNN
11701 NNNNNNNNNN NNNNNNNNNN NNNNNNNNNN NNNNNNNNNN NNNNNNNNNN
11751 NNNNNNNNNN NNNNNNNNNN NNNNNNNNNN NNNNNNNNNN NNNNNNNNNN
11801 NNNNNNNNNN NNNNNNNNNN NNNNNNNNNN NNNNNNNNNN NNNNNNNNNN
11851 NNNNNNNNNN NNNNNNNNNN NNNNNNNNNN NNNNNNNNNN NNNNNNNNNN
11901 NNNNNNNNNN NNNNNNNNNN NNNNNNNNNN NNNNNNNNNN NNNNNNNNNN
11951 NNNNNNNNNN NNNNNNNNNN NNNNNNNNNN NNNNNNNNNN NNNNNNNNNN
12001 NNNNNNNNNN NNNNNNNNNN NNNNNNNNNN NNNNNNNNNN NNNNNNNNNN
12051 NNNNNNNNNN NNNNNNNNNN NNNNNNNNNN NNNNNNNNNN NNNNNNNNNN
12101 NNNNNNNNNN NNNNNNNNNN NNNNNNNNNN NNNNNNNNNN NNNNNNNNNN
12151 NNNNNNNNNN NNNNNNNNNN NNNNNNNNNN NNNNNNNNNN NNNNNNNNNN
12201 NNNNNNNNNN NNNNNNNNNN NNNNNNNNNN NNNNNNNNNN NNNNNNNNNN
12251 NNNNNNNNNN NNNNNNNNNN NNNNNNNNNN NNNNNNNNNN NNNNNNNNNN
12301 NNNNNNNNNN NNNNNNNNNN NNNNNNNNNN NNNNNNNNNN NNNNNNNNNN
12351 NNNNNNNNNN NNNNNNNNNN NNNNNNNNNN NNNNNNNNNN NNNNNNNNNN
12401 NNNNNNNNNN NNNNNNNNNN NNNNNNNNNN NNNNNNNNNN NNNNNNNNNN
12451 NNNNNNNNNN NNNNNNNNNN NNNNNNNNNN NNNNNNNNNN NNNNNNNNNN
12501 NNNNNNNNNN NNNNNNNNNN NNNNNNNNNN NNNNNNNNNN NNNNNNNNNN
12551 NNNNNNNNNN NNNNNNNNNN NNNNNNNNNN NNNNNNNNNN NNNNNNNNNN
12601 NNNNNNNNNN NNNNNNNNNN NNNNNNNNNN NNNNNNNNNN NNNNNNNNNN
12651 NNNNNNNNNN NNNNNNNNNN NNNNNNNNNN NNNNNNNNNN NNNNNNNNNN
12701 NNNNNNNNNN NNNNNNNNNN NNNNNNNNNN NNNNNNNNNN NNNNNNNNNN
12751 NNNNNNNNNN NNNNNNNNNN NNNNNNNNNN NNNNNNNNNN NNNNNNNNNN
12801 NNNNNNNNNN NNNNNNNNNN NNNNNNNNNN NNNNNNNNNN NNNNNNNNNN
12851 NNNNNNNNNN NNNNNNNNNN NNNNNNNNNN NNNNNNNNNN NNNNNNNNNN
12901 NNNNNNNNNN NNNNNNNNNN NNNNNNNNNN NNNNNNNNNN NNNNNNNNNN
12951 NNNNNNNNNN NNNNNNNNNN NNNNNNNNNN NNNNNNNNNN NNNNNNNNNN
13001 NNNNNNNNNN NNNNNNNNNN NNNNNNNNNN NNNNNNNNNN NNNNNNNNNN
13051 NNNNNNNNNN NNNNNNNNNN NNNNNNNNNN NNNNNNNNNN NNNNNNNNNN
13101 NNNNNNNNNN NNNNNNNNNN NNNNNNNNNN NNNNNNNNNN NNNNNNNNNN
13151 NNNNNNNNNN NNNNNNNNNN NNNNNNNNNN NNNNNNNNNN NNNNNNNNNN
13201 NNNNNNNNNN NNNNNNNNNN NNNNNNNNNN NNNNNNNNNN NNNNNNNNNN
13251 NNNNNNNNNN NNNNNNNNNN NNNNNNNNNN NNNNNNNNNN NNNNNNNNNN
13301 NNNNNNNNNN NNNNNNNNNN NNNNNNNNNN NNNNNNNNNN NNNNNNNNNN
13351 NNNNNNNNNN NNNNNNNNNN NNNNNNNNNN NNNNNNNNNN NNNNNNNNNN
13401 NNNNNNNNNN NNNNNNNNNN NNNNNNNNNN NNNNNNNNNN NNNNNNNNNN
13451 NNNNNNNNNN NNNNNNNNNN NNNNNNNNNN NNNNNNNNNN NNNNNNNNNN
```

FIG.3F

```
13501 NNNNNNNNNN NNNNNNNNNN NNNNNNNNNN NNNNNNNNNN NNNNNNNNNN
13551 NNNNNNNNNN NNNNNNNNNN NNNNNNNNNN NNNNNNNNNN NNNNNNNNNN
13601 NNNNNNNNNN NNNNNNNNNN NNNNNNNNNN NNNNNNNNNN NNNNNNNNNN
13651 NNNNNNNNNN NNNNNNNNNN NNNNNNNNNN NNNNNNNNNN NNNNNNNNNN
13701 NNNNNNNNNN NNNNNNNNNN NNNNNNNNNN NNNNNNNNNN NNNNNNNNNN
13751 NNNNNNNNNN NNNNNNNNNN NNNNNNNNNN NNNNNNNNNN NNNNNNNNNN
13801 NNNNNNNNNN NNNNNNNNNN NNNNNNNNNN NNNNNNNNNN NNNNNNNNNN
13851 NNNNNNNNNN NNNNNNNNNN NNNNNNNNNN NNNNNNNNNN NNNNNNNNNN
13901 NNNNNNNNNN NNNNNNNNNN NNNNNNNNNN NNNNNNNNNN NNNNNNNNNN
13951 NNNNNNNNNN NNNNNNNNNN NNNNNNNNNN NNNNNNNNNN NNNNNNNNNN
14001 NNNNNNNNNN NNNNNNNNNN NNNNNNNNNN NNNNNNNNNN NNNNNNNNNN
14051 NNNNNNNNNN NNNNNNNNNN NNNNNNNNNN NNNNNNNNNN NNNNNNNNNN
14101 NNNNNNNNNN NNNNNNNNNN NNNNNNNNNN NNNNNNNNNN NNNNNNNNNN
14151 NNNNNNNNNN NNNNNNNNNN NNNNNNNNNN NNNNNNNNNN NNNNNNNNNN
14201 NNNNNNNNNN NNNNNNNNNN NNNNNNNNNN NNNNNNNNNN NNNNNNNNNN
14251 NNNNNNNNNN NNNNNNNNNN NNNNNNNNNN NNNNNNNNNN NNNNNNNNNN
14301 NNNNNNNNNN NNNNNNNNNN NNNNNNNNNN NNNNNNNNNN NNNNNNNNNN
14351 NNNNNNNNNN NNNNNNNNNN NNNNNNNNNN NNNNNNNNNN NNNNNNNNNN
14401 NNNNNNNNNN NNNNNNNNNN NNNNNNNNNN NNNNNNNNNN NNNNNNNNNN
14451 NNNNNNNNNN NNNNNNNNNN NNNNNNNNNN NNNNNNNNNN NNNNNNNNNN
14501 NNNNNNNNNN NNNNNNNNNN NNNNNNNNNN NNNNNNNNNN NNNNNNNNNN
14551 NNNNNNNNNN NNNNNNNNNN NNNNNNNNNN NNNNNNNNNN NNNNNNNNNN
14601 NNNNNNNNNN NNNNNNNNNN NNNNNNNNNN NNNNNNNNNN NNNNNNNNNN
14651 NNNNNNNNNN NNNNNNNNNN NNNNNNNNNN NNNNNNNNNN NNNNNNNNNN
14701 NNNNNNNNNN NNNNNNNNNN NNNNNNNNNN NNNNNNNNNN NNNNNNNNNN
14751 NNNNNNNNNN NNNNNNNNNN NNNNNNTTTT TGAAAGCTAC TAGTAGGTCA
14801 CCATTTTTTC TTGTCTTCCC GCAATCCAGA CCAGCGCCAC CGCCTCCGAC
14851 AGTGTCCTCG CTCTACCTCT GACCTCTCCG GAGGTTCCGC TGCCTCCAAG
14901 CCGGACTTAG GGCTTCAAGA GGCGGGCGTG CCCTCTGGAG TCCCCTACCA
14951 TGACTGAAGG CGCCAGAGAC TGGCGGTGTC TTAAGACTCC GGGCACCGCC
15001 ACGCGCTGTC AAGCAACACT CTGCGGACCT GCCGGCGTAG TTGCAGCGGG
15051 GGCTTGGGGA GGGGCTGGGG GTTGGACGGG ATTGAGGAAG GTCCGCACAG
15101 CCTGTCTCTG CTCAGTTGCA ATAAACGTGA CATCTTGGGA GCGTTCCCCA
15151 GAGTTTGTCT GCTTCTAGAA CCCGGGTCGC TCCTGCTGCG GTTCCAGGTT
15201 TGGCCGCCAG AAGACGCTGC CGCCTCAGAC GAGGGCGGGC TGTGTGGGGC
15251 GGGAGTACCA GAAAGGGTCG GCGTGTGTCC CCGGGATGCT CGCAGCTTCC
15301 CTCTGCCCAG ACTGGGGTGG CTTTCGGCGC AATCTGTCAA GCTGTTGGAC
15351 CTGCCGTCCC CACTCTGACC ATTGGCTGGG AAAAGTGGAT CTGGCTGATG
15401 CTCCCAGAGC CCAGGAGCCA GGGCGGAGCG GGCGGCGGC TGCTCCCACG
15451 ATCCCAAGGC CGCGCACCTG CCTCCTCCCC CTCCGCCGCC GCCACTTGAG
15501 GGATCGGGAA CAAAGGTGCT TTGTACAGGC CGCAACCACC TCATTACTTC
15551 GTCTTAGGGA CTGGGGCCGC GTGGGCCCCC AGCCCGGAAC GAAGGTGTGG
15601 AGCGGCAAGG GACAGACGCC AATCTTAAAG TGAGCATCTA GCGCGCCACC
15651 TAAGGCTCTT TAGGGAAGGT GGTCCCAGAG CTGTGTTGTC CCTTCCGCTT
15701 GCACTGTCCC TAGATGTGCA AAGAAAACGG GGCAGTGCAT GAAGGTGGTT
```

FIG.3G

```
15751 GGACAGGCTT CATGGATCCT CGCCCGCGCC TCACTTTCCC CTATCTGGGC
15801 AAAGGTTATG TACCCTTATT TAAAATCTTC CAAACTTCTA ATAAGGCAGT
15851 CTACCCTGCA CTAAAGCAGA CACGAAAGAG ATGACCTCCC TAAAAATACT
15901 GCTGTTGGAA TACGTCCTTC CTTCCCGCCC CCTCGCAGTG CGGTGCAGCC
15951 TCAGTGGAAG CTTTGGCGAA CCTGGCGCGC GCTGCGGTGC ACAGAGGGTT
16001 AACTGGAGTT GGCGCTGGGT GGAGAGGAGG AGACGCGCTC CCATTGGCGG
16051 AAAGTTATTC AGGGGCGGGG TCAGTGAATC TCCGTACCCC ACTCCCCTTT
16101 CCGCAACTTC CCTCTTCACT TTGTACCTTT CTCTCCTCGA CTGTGAAGCG
16151 GGCCGGGACC TGCCAGGCCA GACCAAACCG GACCTCGGGG GCGATGCGGC
16201 TGCTGCCCCT GCTGCGGACT GTCCTATGGG CCGCGTCCTC GGCTCCCCTC
16251 TGCGCGGGGG CTCCAGCCTC CGCCACGTAG TCTACTGGAA CTCCAGTAAC
16301 CCCAGGTAGC CGGGCCGAAC CGGGCGAGCG CACAGCCAAG TCTGCGCGCT
16351 CCCGGGCTTT GCGCGCGCCC GCCACCCGCT CTTTGCGCGG CGCCGCCTGA
16401 GCCTGGCCGC GCGCCGGGGC TCCTTTGTTT GAGCCGGCGG GGGAGGGGGG
16451 AGGGGCGAGG GGCGAGGCGC GCCCTGGGTC TCCCCACAGC CCGCATGTGT
16501 TGGGGGGCAG GCAGAAGACC CCAGCCCCAA GGGTTGTCTA GGGGGTCTTG
16551 GAGCATGGAG CTGGGGGGGC CTTTGCCCGC ACTCCGGGCT CCGCCCCCCT
16601 CGCTGCTCTC CTGGCGATCC CCAGCCTCCC GCAGGCTGGA GCTGTGGCTG
16651 ACGAACTTGA GAGCGAGGGA GGGGGCTTTA CTCTTATGAA AGAGCGTGGG
16701 TTACTCTCCT GCCCGCTGGG TCTCACCTCT GGCTCTCACT CTGTCTCCTG
16751 ATCTCATTTG CTATCTCTGC TTTCATCTCT GTCTTTATTG GTCCTTCTGT
16801 TTCTTTCCAG TGTCAGCCCT GCCCTTCTAG CCGAATCACC TCTGGGCAAG
16851 TCTCGTGACC TTCCTAACCT CATTTATCTC ACCTGTATAA TGGGCTAATA
16901 ATACCTAGTA CCCTGGGAAG TCTGGCAGGG TAAGTGAGGT CATGTATGTG
16951 AAAGAGGCTC AGGCTGTACA GATATAAACT ATTATTTCTT TCTCTCTCCT
17001 GAGCTGCCTG CCTTTGAACC TTAGTATATT TTACTGTTTC CATCCCCCTC
17051 CCCAAGTCTC CCTGCCTCTC CTATTTCCTA TCTGTTTTTC TTTCTGATTT
17101 TCTACTTGAG ACAATCTGTG ACTATTCATT TCTTCACT
    (SEQ ID NO: 3)
```

FEATURES:
Start: 2076
Exon:    2076-2154
Intron:  2155-3308
Exon:    3309-3466
Intron:  3467-4104
Exon:    4105-4181
Intron:  4182-4206
Exon:    4207-4250
Intron:  4251-4436
Exon:    4437-4607
Intron:  4608-5048
Exon:    5049-5052
Intron:  5053-6007
Exon:    6008-6145

FIG.3H

Intron:    6146-6528
Exon:      6529-6589
Intron:    6590-6668
Exon:      6669-6737
Intron:    6738-6816
Exon:      6817-6986
Intron:    6987-7122
Exon:      7123-7207
Intron:    7208-7689
Exon:      7690-7838
Intron:    7839-7943
Exon:      7944-8118
Intron:    8119-8392
Exon:      8393-8485
Intron:    8486-8606
Exon:      8607-8911
Intron:    8912-9248
Exon:      9249-9444
Intron:    9445-9712
Exon:      9713-9791
Stop 9792

SNPs:

| DNA Position | Major | Minor | Domain | Protein Position | Major | Minor |
|---|---|---|---|---|---|---|
| 2522 | C | G | Intron | | | |
| 4326 | C | T | Intron | | | |
| 5954 | T | - | Intron | | | |
| 6783 | G | A | Intron | | | |
| 7514 | A | C | Intron | | | |
| 15505 | C | T | Beyond ORF(3') | | | |
| 16123 | A | G | Beyond ORF(3') | | | |

Context:

DNA Position

2522    TTAGGGTAATGGGGCCGGACGGAGACCCTGGGAGAGCCCAGCCAGAGCGCGGCCCGCCCT
        GGTCCGCTGTCCTGGGCCTAGGGCCCGGTGACTTGGCGATGGGGTGAAAAGAGAAGGAGG
        GGGGATGCCGGCGCCCCCTGCCTCCTGCCTGGTCATCCTCTGCGCGGTCCCTGCGGACAC
        TTTCAGGCTCAGGTACCAGGTACCGAGGGGCCTGTCCAGCGCCACTTCAAGATCGTGATG

FIG.31

AGAGGGTCGCTGCTCCCCAGGACTGGCATCTTCGCTGCTCTGGGGCCTAGCTAACCGTTC
[C,G]
ACCCGGTGCCAGGGCGCTGAGCGGGCATGGCTTGTAGGGTTTAGTGAAGAGGATTCTCTC
TAGCCTCTATTCCAGGCCTGGGGCCGCCAGGCACTCCTCACCCTGGTGCTGTTGCCACCA
GTGCCTGGCCGAGCGGGAGGGGCCCGAGATGAGCCAGGAGAAGGGAGAATTGGCCAGGAA
AGAGGCTGGGACACCAACTCCTCCTTGGAACTTTCACTTCCCGCTGCTGTCTTGGGCCGG
GACCGAGAGGGCAGGCGCGGGTGGAGTGTCCGGAGGAGAGAGGGCCATTGTGTGTTGGGG

4326    GGGCCTGAGGTTTTCTGGTTAGAGAGGCTGGGAGTTGTGGACAGGTCTAGGGAGGTGACC
TGCCCTCTGGTGCCCACAGACCAGTCTGCCTGAGCCCCTGAGGATCAAGTTGGAGCTGGA
CGGTGACAGTCATATCCTGGAGCTGCTACAGAATAGGTAATAGTGATGGTGGCAATAACA
GTGACCACATGGCCAACAACTTGTATAGCATTTATTATGTGCCAGGTACTAAGTGCTTGT
GCTCATTTAATCCTCATAACAGCCCTATAAGGGATATACTATCATGTATTATTGTCCTCA
[C,T]
TTTATACATGAGGAAGTCAAGGCACAGAGAGATTAAATAACTTGCCCCAGGTCACACAGC
TAGTATGTGGTGAAAACCAGATTGGAATTCAAATAAACTAACAGAGTCAGTGGCCCAACC
AGTATACTTTGCTGCCCCGGGGTCAGGAGTGGAAAAGTTGGCTGCGGGGGTTGCCTGGTC
CCCAGCCCCACAACCACCTTCAAGCCTCTGCTTGTCAATGCACCGACCCTGGGAAGTGGC
TTTAGCACTGCCTTCTTTTTCTTCACTTCACAGGGGAGTTGGTCCCATGTCCGCCCCGAC

5954    AGGTGGTTTGCCCGAGGCCCTACAACTAATAAATGGCCTATCCATTTATTAGTTGTATTT
GGCTCTTCATCTGTCTTATGATCCCATTTGCAGAGAGCTCTCACTTGGTTATAGATAATA
CATAGTTACCAATGATGAAGCAATATAAACCCAATTTCCTAATTTGTAAAATGAAGATAA
TAAAACTACTTGCTGCATAGAGTTGCTGGGAAGATTAAATAAGTCCATATAGATGTAAAG
TGCTTAAAACTATGCCAGACCTATGGTAAGTGACAAGAGTTGTTATTGGGATTTTTAAAA
[T,-]
TATTATTATTATTATTATTATTTGAGACAGAGTCTCGCTCTGTCTCCCAGGCTGGAG
TGCAGTGGCGTGATCTCGGCTCACTGCAAGCTCCGCCTCCCAGGTTCACGCCATTCTCTT
GCCTCAGCCTCCCGAGTAGCTGGGACTACAGGCGCCCGCCACTACACCCGGCTAATGTTT
TGTATTTTTTAGTACAGACAGGGTTTCACCGTGTTATCCAGGATGGTCTCGATCTCCTGA
CCTCATGATCCACCCGCCTTGTCCTCCCAAAGTGCTGAGATTACAGGCGTGAGCCACCGC

6783    TGCGAGCGGCAGGTTTGCCTGATAATTCTTCTTGTCCATAGTAGAGGCGGGATGTGGTAA
CAGAGACCAAGACTGTGGAGTTGGTGATTGTGGCTGATCACTCGGAGGTGAGCCTGCTGG
CCCCTGCACATCCTCCTCCCCCTGCACTGCCCTGCCGCCTTTCATGTCACCTCTCTTGGC
CTACAGGCCCAGAAATACCGGGACTTCCAGCACCTGCTAAACCGCACACTGGAAGTGGCC
CTCTTGCTGGACACAGTGAGTGCTGGACAGGGCAACCCCCACCCCAGGCCCCTGACCATG
[G,A]
CAACCCCTCTTCTGAGCCCCAGCTGTCTTTCAGTTCTTCCGGCCCCTGAATGTACGAGTG
GCACTAGTGGGCCTGGAGGCCTGGACCCAGCGTGACCTGGTGGAGATCAGCCCAAACCCA
GCTGTCACCCTCGAAAACTTCCTCCACTGGCGCAGGGCACATTTGCTGCCTCGATTGCCC
CATGACAGTGCCCAGCTGGTGACGTAAGGGCCCCAGACTCAGCCAGAGAGGCCAGTCCTG
TCCTGGCCAAATTCACACCCCTTCAGCACCCTACCTCAGCCCCTGAAGCTCTGACCACCG

7514    TATTTCCAGGTCTCCTCCTCATTCCCAATTCAGTTCCTCCCAAGTGTGGTGGCATTTATG

FIG.3J

```
        CACTGAAACCCCCCTATAAAGTTGCCCAACCCCAAAGCTACAGGTATAGAGGGTGGAGGT
        ACGTGATGTGGCCTTTGCTATCAGGGAGCCCTCGCTTATGGCCAGCTAGTCACAGTGTAC
        ACAGTCATCCCCTGTGCAGTCTTCCCATTTCTTAGAGGAGGGTAGGAGGCAGCTAAGGCC
        CAAAGAACAGAGGTGATCTCCCTCCAGTGAGGGAGGGGGACAGAGCTGAGCTAGAACCCA
        [A,C]
        GTTTCTGCCATCCAGGCCTGGGTTCTCCTACTTTAGAAGCAATTCAGGAGGGAAGCAGTG
        CCTGCTGAGTGCCCACGAGGTCAGACGTGGAGGGAACAGGAGCAGAGAGGGTGGTCTGGG
        CATTGTGGTGGAGGCAGGCTGGGACTGGACCTACAGTACCCCTCCCCAATGACAGGACCA
        CTCCACCAGCATCCTGGGAGTCGCCTCCTCCATAGCCCATGAGTTGGGCCACAGCCTGGG
        CCTGGACCATGATTTGCCTGGGAATAGCTGCCCCTGTCCAGGTCCAGCCCCAGCCAAGAC

15505   CGCCAGAAGACGCTGCCGCCTCAGACGAGGGCGGGCTGTGTGGGGCGGGAGTACCAGAAA
        GGGTCGGCGTGTGTCCCCGGGATGCTCGCAGCTTCCCTCTGCCCAGACTGGGGTGGCTTT
        CGGCGCAATCTGTCAAGCTGTTGGACCTGCCGTCCCCACTCTGACCATTGGCTGGGAAAA
        GTGGATCTGGCTGATGCTCCCAGAGCCCAGGAGCCAGGGCGGAGCGGGGCGGCGGCTGCT
        CCCACGATCCCAAGGCCGCGCACCTGCCTCCTCCCCCTCCGCCGCCGCCACTTGAGGGAT
        [C,T]
        GGGAACAAAGGTGCTTTGTACAGGCCGCAACCACCTCATTACTTCGTCTTAGGGACTGGG
        GCCGCGTGGGCCCCCAGCCCGGAACGAAGGTGTGGAGCGGCAAGGGACAGACGCCAATCT
        TAAAGTGAGCATCTAGCGCGCCACCTAAGGCTCTTTAGGGAAGGTGGTCCCAGAGCTGTG
        TTGTCCCTTCCGCTTGCACTGTCCCTAGATGTGCAAAGAAAACGGGGCAGTGCATGAAGG
        TGGTTGGACAGGCTTCATGGATCCTCGCCCGCGCCTCACTTTCCCCTATCTGGGCAAAGG

16123   AAATCTTCCAAACTTCTAATAAGGCAGTCTACCCTGCACTAAAGCAGACACGAAAGAGAT
        GACCTCCCTAAAAATACTGCTGTTGGAATACGTCCTTCCTTCCCGCCCCCTCGCAGTGCG
        GTGCAGCCTCAGTGGAAGCTTTGGCGAACCTGGCGCGCGCTGCGGTGCACAGAGGGTTAA
        CTGGAGTTGGCGCTGGGTGGAGAGGAGGAGACGCGCTCCCATTGGCGGAAAGTTATTCAG
        GGGCGGGGTCAGTGAATCTCCGTACCCCACTCCCCTTTCCGCAACTTCCCTCTTCACTTT
        [A,G]
        TACCTTTCTCTCCTCGACTGTGAAGCGGGCCGGGACCTGCCAGGCCAGACCAAACCGGAC
        CTCGGGGGCGATGCGGCTGCTGCCCCTGCTGCGGACTGTCCTATGGGCCGCGTCCTCGGC
        TCCCCTCTGCGCGGGGGCTCCAGCCTCCGCCACGTAGTCTACTGGAACTCCAGTAACCCC
        AGGTAGCCGGGCCGAACCGGGCGAGCGCACAGCCAAGTCTGCGCGCTCCCGGGCTTTGCG
        CGCGCCCGCCACCCGCTCTTTGCGCGGCGCCGCCTGAGCCTGGCCGCGCGCCGGGGCTCC
Chromosome map:
Chromosome # 1
```

FIG.3K

ISOLATED HUMAN METALLOPROTEASE PROTEINS, NUCLEIC ACID MOLECULES ENCODING HUMAN PROTEASE PROTEINS, AND USES THEREOF

FIELD OF THE INVENTION

The present invention is in the field of protease proteins that are related to the metalloprotease subfamily, recombinant DNA molecules, and protein production. The present invention specifically provides novel peptides and proteins that effect protein cleavage/processing/turnover and nucleic acid molecules encoding such peptide and protein molecules, all of which are useful in the development of human therapeutics and diagnostic compositions and methods.

BACKGROUND OF THE INVENTION

The proteases may be categorized into families by the different amino acid sequences (generally between 2 and 10 residues) located on either side of the cleavage site of the protease.

The proper functioning of the cell requires careful control of the levels of important structural proteins, enzymes, and regulatory proteins. One of the ways that cells can reduce the steady state level of a particular protein is by proteolytic degradation. Further, one of the ways cells produce functioning proteins is to produce pre or pro-protein precursors that are processed by proteolytic degradation to produce an active moiety. Thus, complex and highly-regulated mechanisms have been evolved to accomplish this degradation.

Proteases regulate many different cell proliferation, differentiation, and signaling processes by regulating protein turnover and processing. Uncontrolled protease activity (either increased or decreased) has been implicated in a variety of disease conditions including inflammation, cancer, arteriosclerosis, and degenerative disorders.

An additional role of intracellular proteolysis is in the stress-response. Cells that are subject to stress such as starvation, heat-shock, chemical insult or mutation respond by increasing the rates of proteolysis. One function of this enhanced proteolysis is to salvage amino acids from non-essential proteins. These amino acids can then be re-utilized in the synthesis of essential proteins or metabolized directly to provide energy. Another function is in the repair of damage caused by the stress. For example, oxidative stress has been shown to damage a variety of proteins and cause them to be rapidly degraded.

The International Union of Biochemistry and Molecular Biology (IUBMB) has recommended to use the term peptidase for the subset of peptide bond hydrolases (Subclass E.C 3.4.). The widely used term protease is synonymous with peptidase. Peptidases comprise two groups of enzymes: the endopeptidases and the exopeptidases, which cleave peptide bonds at points within the protein and remove amino acids sequentially from either N or C-terminus respectively. The term proteinase is also used as a synonym word for endopeptidase and four mechanistic classes of proteinases are recognized by the IUBMB: two of these are described below (also see: *Handbook of Proteolytic Enzymes* by Barrett, Rawlings, and Woessner AP Press, N.Y. 1998). Also, for a review of the various uses of proteases as drug targets, see: Weber M, Emerging treatments for hypertension: potential role for vasopeptidase inhibition; Am J Hypertens Nov. 12, 1999 (11 Pt 2):139S–147S; Kentsch M, Otter W, Novel neurohormonal modulators in cardiovascular disorders. The therapeutic potential of endopeptidase inhibitors, Drugs R D Apr. 1, 1999 (4):331–8; Scarborough R M, Coagulation factor Xa: the prothrombinase complex as an emerging therapeutic target for small molecule inhibitors, J Enzym Inhib 1998;14(1):15–25; Skotnicki J S, et al., Design and synthetic considerations of matrix metalloproteinase inhibitors, Ann N Y Acad Sci Jun. 30, 1999 878:61–72; McKerrow J H, Engel J C, Caffrey C R, Cysteine protease inhibitors as chemotherapy for parasitic infections, Bioorg Med Chem Apr. 7, 1999 (4):639–44; Rice K D, Tanaka R D, Katz B A, Numerof R P, Moore W R, Inhibitors of tryptase for the treatment of mast cell-mediated diseases, Curr Pharm Des Oct. 4, 1998 (5):381–96; Materson B J, Will angiotensin converting enzyme genotype, receptor mutation identification, and other miracles of molecular biology permit reduction of NNT Am J Hypertens Aug. 11, 1998 (8 Pt2):138S–142S Serine Proteases The serine proteases (SP) are a large family of proteolytic enzymes that include the digestive enzymes, trypsin and chymotrypsin, components of the complement cascade and of the blood-clotting cascade, and enzymes that control the degradation and turnover of macromolecules of the extra-cellular matrix. SP are so named because of the presence of a serine residue in the active catalytic site for protein cleavage. SP have a wide range of substrate specificities and can be subdivided into subfamilies on the basis of these specificities. The main sub-families are trypases (cleavage after arginine or lysine), aspases (cleavage after aspartate), chymases (cleavage after phenylalanine or leucine), metases (cleavage after methionine), and serases (cleavage after serine).

A series of six SP have been identified in murine cytotoxic T-lymphocytes (CTL) and natural killer (NK) cells. These SP are involved with CTL and NK cells in the destruction of virally transformed cells and tumor cells and in organ and tissue transplant rejection (Zunino, S. J. et al. (1990) J. Immunol. 144:2001–9; Sayers, T. J. et al. (1994) J. Immunol. 152:2289–97). Human homologs of most of these enzymes have been identified (Trapani, J. A. et al. (1988) Proc. Natl. Acad. Sci. 85:6924–28; Caputo, A. et al. (1990) J. Immunol. 145:737–44). Like all SP, the CTL-SP share three distinguishing features: 1) the presence of a catalytic triad of histidine, serine, and aspartate residues which comprise the active site; 2) the sequence GDSGGP which contains the active site serine; and 3) an N-terminal IIGG sequence which characterizes the mature SP.

The SP are secretory proteins which contain N-terminal signal peptides that serve to export the immature protein across the endoplasmic reticulum and are then cleaved (von Heijne (1986) Nuc. Acid. Res. 14:5683–90). Differences in these signal sequences provide one means of distinguishing individual SP. Some SP, particularly the digestive enzymes, exist as inactive precursors or preproenzymes, and contain a leader or activation peptide sequence 3' of the signal peptide. This activation peptide may be 2–12 amino acids in length, and it extends from the cleavage site of the signal peptide to the N-terminal IIGG sequence of the active, mature protein. Cleavage of this sequence activates the enzyme. This sequence varies in different SP according to the biochemical pathway and/or its substrate (Zunino et al, supra; Sayers et al, supra). Other features that distinguish various SP are the presence or absence of N-linked glycosylation sites that provide membrane anchors, the number and distribution of cysteine residues that determine the secondary structure of the SP, and the sequence of a substrate binding sites such as S'. The S' substrate binding region is defined by residues extending from approximately +17 to +29 relative to the N-terminal I (+1). Differences in this region of the molecule are believed to determine SP substrate specificities (Zunino et al, supra).

Trypsinogens

The trypsinogens are serine proteases secreted by exocrine cells of the pancreas (Travis J and Roberts R. Biochemistry 1969; 8: 2884–9; Mallory P and Travis J, Biochemistry 1973; 12: 2847–51). Two major types of trypsinogen isoenzymes have been characterized, trypsinogen-1, also called cationic trypsinogen, and trypsinogen-2 or anionic trypsinogen. The trypsinogen proenzymes are activated to trypsins in the intestine by enterokinase, which removes an activation peptide from the N-terminus of the trypsinogens. The trypsinogens show a high degree of sequence homology, but they can be separated on the basis of charge differences by using electrophoresis or ion exchange chromatography. The major form of trypsinogen in the pancreas and pancreatic juice is trypsinogen-1 (Guy C O et al., Biochem Biophys Res Commun 1984; 125: 516–23). In serum of healthy subjects, trypsinogen-1 is also the major form, whereas in patients with pancreatitis, trypsinogen-2 is more strongly elevated (Itkonen et al., J Lab Clin Med 1990; 115:712–8). Trypsinogens also occur in certain ovarian tumors, in which trypsinogen-2 is the major form (Koivunen et al., Cancer Res 1990; 50: 2375–8). Trypsin-1 in complex with alpha-1-antitrypsin, also called alpha-1-antiprotease, has been found to occur in serum of patients with pancreatitis (Borgstrom A and Ohlsson K, Scand J Clin Lab Invest 1984; 44: 381–6) but determination of this complex has not been found useful for differentiation between pancreatic and other gastrointestinal diseases (Borgstrom et al., Scand J Clin Lab Invest 1989; 49:757–62).

Trypsinogen-1 and -2 are closely related immunologically (Kimland et al., Clin Chim Acta 1989; 184: 31–46; Itkonen et al., 1990), but by using monoclonal antibodies (Itkonen et al., 1990) or by absorbing polyclonal antisera (Kimland et al., 1989) it is possible to obtain reagents enabling specific measurement of each form of trypsinogen.

When active trypsin reaches the blood stream, it is inactivated by the major trypsin inhibitors alpha-2-macroglobulin and alpha-1-antitrypsin (AAT). AAT is a 58 kilodalton serine protease inhibitor synthesized in the liver and is one of the main protease inhibitors in blood. Whereas complexes between trypsin-1 and AAT are detectable in serum (Borgstrom and Ohlsson, 1984) the complexes with alpha -2-macroglobulin are not measurable with antibody-based assays (Ohlsson K, Acta Gastroenterol Belg 1988; 51: 3–12).

Inflammation of the pancreas or pancreatitis may be classified as either acute or chronic by clinical criteria. With treatment, acute pancreatitis can often be cured and normal function restored. Chronic pancreatitis often results in permanent damage. The precise mechanisms which trigger acute inflammation are not understood. However, some causes in the order of their importance are alcohol ingestion, biliary tract disease, post-operative trauma, and hereditary pancreatitis. One theory provides that autodigestion, the premature activation of proteolytic enzymes in the pancreas rather than in the duodenum, causes acute pancreatitis. Any number of other factors including endotoxins, exotoxins, viral infections, ischemia, anoxia, and direct trauma may activate the proenzymes. In addition, any internal or external blockage of pancreatic ducts can also cause an accumulation of pancreatic juices in the pancreas resulting cellular damage.

Anatomy, physiology, and diseases of the pancreas are reviewed, inter alia, in Guyton A C (1991) Textbook of Medical Physiology, W B Saunders Co, Philadelphia Pa.; Isselbacher K J et al (1994) Harrison's Principles of Internal Medicine, McGraw-Hill, New York City; Johnson K E (1991) Histology and Cell Biology, Harwal Publishing, Media Pa.; and The Merck Manual of Diagnosis and Therapy (1992) Merck Research Laboratories, Rahway N.J.

Aspartic protease

Aspartic proteases have been divided into several distinct families based primarily on activity and structure. These include 1) water nucleophile; water bound by two Asp from monomer or dimer; all endopeptidases, from eukaryote organisms, viruses or virus-like organisms and 2) endopeptidases that are water nucleophile and are water bound by Asp and Asn.

Most of aspartic proteases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral proteases such as the protease from the AIDS virus (HIV) also called retropepsin. Crystallographic studies have shown that these enzymes are bilobed molecules with the active site located between two homologous lobes. Each lobe contributes one aspartate residue of the catalytically active diad of aspartates. These two aspartyl residues are in close geometric proximity in the active molecule and one aspartate is ionized whereas the second one is unionized at the optimum pH range of 2–3. Retropepsins, are monomeric, i.e carry only one catalytic aspartate and then dimerization is required to form an active enzyme.

In contrast to serine and cysteine proteases, catalysis by aspartic protease do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO—NH bond cleavage. This general acid-base catalysis, which may be called a "push-pull" mechanism leads to the formation of a non covalent neutral tetrahedral intermediate.

Examples of the aspartic protease family of proteins include, but are not limited to, pepsin A (*Homo sapiens*), HIV1 retropepsin (human immunodeficiency virus type 1), endopeptidase (cauliflower mosaic virus), bacilliform virus putative protease (rice tungro bacilliform virus), aspergillopepsin II (*Aspergillus niger*), thermopsin (*Sulfolobus acidocaldarius*), nodavirus endopeptidase (flock house virus), pseudomonapepsin (Pseudomonas sp. 101), signal peptidase II (*Escherichia coli*), polyprotein peptidase (human spumaretrovirus), copia transposon (*Drosophila melanogaster*), SIRE-1 peptidase (*Glycine max*), retrotransposon bs1 endopeptidase (*Zea mays*), retrotransposon peptidase (*Drosophila buzzatii*), Tas retrotransposon peptidase (*Ascaris lumbricoides*), Pao retrotransposon peptidase (*Bombyx mori*), putative proteinase of Skippy retrotransposon (*Fusarium oxysporum*), tetravirus endopeptidase (*Nudaurelia capensis* omega virus), presenilin 1 (*Homo sapiens*).

Metalloprotease

The metalloproteases may be one of the older classes of proteinases and are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Metalloproteases contain a catalytic zinc metal center which participates in the hydrolysis of the peptide backbone (reviewed in Power and Harper, in Protease Inhibitors, A. J. Barrett and G. Salversen (eds.) Elsevier, Amsterdam, 1986, p. 219). The active zinc center differentiates some of these proteases from calpains and trypsins whose activities are dependent upon the presence of calcium. Examples of metalloproteases include carboxypeptidase A, carboxypeptidase B, and thermolysin.

Metalloproteases have been isolated from a number of procaryotic and eucaryotic sources, e.g. *Bacillus subtilis* (McConn et al., 1964, J. Biol. Chem. 239:3706); *Bacillus megaterium;* Serratia (Miyata et al., 1971, Agr. Biol. Chem. 35:460); *Clostridium bifermentans* (MacFarlane et al., 1992, App. Environ. Microbiol. 58:1195–1200), *Legionella pneumophila* (Moffat et al., 1994, Infection and Immunity 62:751–3). In particular, acidic metalloproteases have been isolated from broad-banded copperhead venoms (Johnson and Ownby, 1993, Int. J. Biochem. 25:267–278), rattlesnake venoms (Chlou et al., 1992, Biochem. Biophys. Res. Commun. 187:389–396) and articular cartilage (Treadwell et al., 1986, Arch. Biochem. Biophys. 251:715–723). Neutral metalloproteases, specifically those having optimal activity at neutral pH. have for example, been isolated from *Aspergillus sojae* (Sekine, 1973, Agric. Biol. Chem. 37:1945–1952). Neutral metalloproteases obtained from Aspergillus have been classified into two groups, npI and npII (Sekine, 1972, Agric. Biol. Chem. 36:207–216). So far, success in obtaining amino acid sequence information from these fungal neutral metalloproteases has been limited. An npII metalloprotease isolated from *Aspergillus oryzae* has been cloned based on amino acid sequence presented in the literature (Tatsumi et al., 1991, Mol. Gen. Genet. 228:97–103). However, to date, no npI fungal metalloprotease has been cloned or sequenced. Alkaline metalloproteases, for example, have been isolated from *Pseudomonas aeruginosa* (Baumann et al., 1993, EMBO J 12:3357–3364) and the insect pathogen *Xenorhabdus luminescens* (Schmidt et al., 1998, Appl. Environ. Microbiol. 54:2793–2797).

Metalloproteases have been devided into several distinct families based primarily on activity and sturcture: 1) water nucleophile; water bound by single zinc ion ligated to two His (within the motif HEXXH) and Glu, His or Asp; 2) water nucleophile; water bound by single zinc ion ligated to His, Glu (within the motif HXXE) and His; 3) water nucleophile; water bound by single zinc ion ligated to His, Asp and His; 4) Water nucleophile; water bound by single zinc ion ligated to two His (within the motif HXXEH) and Glu and 5) water nucleophile; water bound by two zinc ions ligated by Lys, Asp, Asp, Asp, Glu.

Examples of members of the metalloproteinase family include, but are not limited to, membrane alanyl aminopeptidase (*Homo sapiens*), germinal peptidyl-dipeptidase A (*Homo sapiens*), thimet oligopeptidase (*Rattus norvegicus*), oligopeptidase F (*Lactococcus lactis*), mycolysin (*Streptomyces cacaoi*), immune inhibitor A (*Bacillus thuringiensis*), snapalysin (*Streptomyces lividans*), leishmanolysin (*Leishmania major*), microbial collagenase (*Vibrio alginolyticus*), microbial collagenase, class I (*Clostridium perfringens*), collagenase 1 (*Homo sapiens*), serralysin (*Serratia marcescens*), fragilysin (*Bacteroides fragilis*), gametolysin (*Chlamydomonas reinhardtii*), astacin (*Astacus fluviatilis*), adamalysin (*Crotalus adamanteus*), ADAM 10 (*Bos taurus*), neprilysin (*Homo sapiens*), carboxypeptidase A (*Homo sapiens*), carboxypeptidase E (*Bos taurus*), gamma-D-glutamyl-(L)-meso-diaminopimelate peptidase I (*Bacillus sphaericus*), vanY D-Ala-D-Ala carboxypeptidase (*Enterococcus faecium*), endolysin (bacteriophage A118), pitrilysin (*Escherichia coli*), mitochondrial processing peptidase (*Saccharomyces cerevisiae*), leucyl aminopeptidase (*Bos taurus*), aminopeptidase I (*Saccharomyces cerevisiae*), membrane dipeptidase (*Homo sapiens*), glutamate carboxypeptidase (Pseudomonas sp.), Gly-X carboxypeptidase (*Saccharomyces cerevisiae*), O-sialoglycoprotein endopeptidase (*Pasteurella haemolytica*), beta-lytic metalloendopeptidase (*Achromobacter lyticus*), methionyl aminopeptidase I (*Escherichia coli*), X-Pro aminopeptidase (*Escherichia coli*), X-His dipeptidase (*Escherichia coli*), IgA1-specific metalloendopeptidase (*Streptococcus sanguis*), tentoxilysin (*Clostridium tetani*), leucyl aminopeptidase (*Vibrio proteolyticus*), aminopeptidase (*Streptomyces griseus*), IAP aminopeptidase (*Escherichia coli*), aminopeptidase T (*Thermus aquaticus*), hyicolysin (*Staphylococcus hyicus*), carboxypeptidase Taq (*Thermus aquaticus*), anthrax lethal factor (*Bacillus anthracis*), penicillolysin (*Penicillium citrinum*), fungalysin (*Aspergillus fumigatus*), lysostaphin (*Staphylococcus simulans*), beta-aspartyl dipeptidase (*Escherichia coli*), carboxypeptidase Ss1 (*Sulfolobus solfataricus*), FtsH endopeptidase (*Escherichia coli*), glutamyl aminopeptidase (*Lactococcus lactis*), cytophagalysin (Cytophaga sp.), metalloendopeptidase (vaccinia virus), VanX D-Ala-D-Ala dipeptidase (*Enterococcus faecium*), Ste24p endopeptidase (*Saccharomyces cerevisiae*), dipeptidyl-peptidase III (*Rattus norvegicus*), S2P protease (*Homo sapiens*), sporulation factor SpoIVFB (*Bacillus subtilis*), and HYBD endopeptidase (*Escherichia coli*).

Metalloproteases have been found to have a number of uses. For example, there is strong evidence that a metalloprotease is involved in the in vivo proteolytic processing of the vasoconstrictor, endothelin-1. Rat metalloprotease has been found to be involved in peptide hormone processing. One important subfamily of the metalloproteases are the matrix metalloproteases.

A number of diseases are thought to be mediated by excess or undesired metalloprotease activity or by an imbalance in the ratio of the various members of the protease family of proteins. These include: a) osteoarthritis (Woessner, et al., J. Biol.Chem. 259(6), 3633, 1984; Phadke, et al., J. Rheumatol. 10, 852, 1983), b) rheumatoid arthritis (Mullins, et al., Biochim. Biophys. Acta 695, 117, 1983; Woolley, et al., Arthritis Rheum. 20, 1231, 1977; Gravallese, et al., Arthritis Rheum. 34, 1076, 1991), c) septic arthritis (Williams, et al., Arthritis Rheum. 33, 533, 1990), d) periodontal diseases (Overall, et al., J. Periodontal Res. 22, 81, 1987), e) corneal ulceration (Bums, et al., Invest. Opthalmol. Vis. Sci. 30, 1569, 1989), f) proteinuria (Baricos, et al., Biochem. J. 254, 609, 1988), g) coronary thrombosis from atherosclerotic plaque rupture (Henney, et al., Proc. Nat'l. Acad. Sci., USA 88, 8154–8158, 1991), h) aneurysmal aortic disease (Vine, et al., Clin. Sci. 81, 233, 1991), i) birth control (Woessner, et al., Steroids 54, 491, 1989), j) dystrophobic epidermolysis bullosa (Kronberger, et al., J. Invest. Dermatol. 79, 208, 1982), and k) degenerative cartilage loss following traumatic joint injury, l) conditions leading to inflammatory responses, osteopenias mediated by MMP activity, m) tempero mandibular joint disease, n) demyelating diseases of the nervous system (Chantry, et al., J. Neurochem. 50, 688, 1988).

The present invention has a substantial similarity with metalloproteinase/disintegrin family termed ADAM. ADAM protein was isolated from myeloma cells, bovine brain or mammary derived epithelial cells. Northern blotting was used to confirm expression. Chondrocytes were an important source of metalloproteinase enzymes involved in joint pathology the potential relevance of the expression of these molecules to connective tissue disorders.

The ADAMs (a disintegrin and metalloprotease domain) are a family of type I transmembrane glycoproteins that are important in diverse biologic processes, such as cell adhesion and proteolytic shedding of cell surface receptors. Structurally, ADAMs consist of a prodomain that blocks protease activity; a zinc-binding metalloprotease domain; disintegrin and cysteine-rich domains with adhesion activity; an epidermal growth factor-like domain with cell fusion activity; a transmembrane domain; and a phosphorylated cytoplasmic regulatory domain.

For references related to metalloprotease, see review of McKie et al., Biochem Biophys Res Commun Jan. 13, 1997;230(2):335–9; Herren et al., FASEB J. 11: 173–180, 1997; Karkkainen et al., Cell Genet. 88: 206–207, 2000; Kratzschmar et al., J. Biol. Chem. 271: 4593–4596, 1996; Nath et al., J. Cell Sci. 112: 579–587, 1999; Primakoff et al., Trends Genet. 16: 83–87, 2000; Zhang et al., J. Biol. Chem. 273: 7345–7350, 1998.

Protease proteins, particularly members of the metalloprotease subfamily, are a major target for drug action and development. Accordingly, it is valuable to the field of pharmaceutical development to identify and characterize previously unknown members of this subfamily of protease proteins. The present invention advances the state of the art by providing a previously unidentified human protease proteins that have homology to members of the metalloprotease subfamily.

SUMMARY OF THE INVENTION

The present invention is based in part on the identification of amino acid sequences of human protease peptides and proteins that are related to the metalloprotease subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate protease activity in cells and tissues that express the protease. Experimental data as provided in FIG. 1 indicates expression in the placenta, lung, ovary, colon, kidney, thyroid gland, prostate, eye and leucocyte.

DESCRIPTION OF THE FIGURE SHEETS

FIG. 1 provides the nucleotide sequence of a cDNA molecule sequence that encodes the protease protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the placenta, lung, ovary, colon, kidney, thyroid gland, prostate, eye and leucocyte.

FIG. 2 provides the predicted amino acid sequence of the protease of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the protease protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs, including insertion/deletion variants ("indels"), were identified at 7 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a protease protein or part of a protease protein and are related to the metalloprotease subfamily. Utilizing these sequences, additional genomic sequences were assembled and transcript and/or cDNA sequences were isolated and characterized. Based on this analysis, the present invention provides amino acid sequences of human protease peptides and proteins that are related to the metalloprotease subfamily, nucleic acid sequences in the form of transcript sequences, cDNA sequences and/or genomic sequences that encode these protease peptides and proteins, nucleic acid variation (allelic information), tissue distribution of expression, and information about the closest art known protein/peptide/domain that has structural or sequence homology to the protease of the present invention.

In addition to being previously unknown, the peptides that are provided in the present invention are selected based on their ability to be used for the development of commercially important products and services. Specifically, the present peptides are selected based on homology and/or structural relatedness to known protease proteins of the metalloprotease subfamily and the expression pattern observed. Experimental data as provided in FIG. 1 indicates expression in the placenta, lung, ovary, colon, kidney, thyroid gland, prostate, eye and leucocyte. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known metalloprotease family or subfamily of protease proteins.

Specific Embodiments

Peptide Molecules

The present invention provides nucleic acid sequences that encode protein molecules that have been identified as being members of the protease family of proteins and are related to the metalloprotease subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the protease peptides of the present invention, protease peptides, or peptides/proteins of the present invention.

The present invention provides isolated peptide and protein molecules that consist of, consist essentially of, or comprise the amino acid sequences of the protease peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the protease peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated protease peptide can be purified from cells that naturally express it, purified from cells that have been altered to express it (recombinant), or synthesized using known protein synthesis methods. Experimental data as provided in FIG. 1 indicates expression in the placenta, lung, ovary, colon, kidney, thyroid gland, prostate, eye and leucocyte. For example, a nucleic acid molecule encoding the protease peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the protease peptides of the present invention are the naturally occurring mature proteins. A brief description of how various types of these proteins can be made/isolated is provided below.

The protease peptides of the present invention can be attached to heterologous sequences to form chimeric or fusion proteins. Such chimeric and fusion proteins comprise a protease peptide operatively linked to a heterologous protein having an amino acid sequence not substantially homologous to the protease peptide. "Operatively linked" indicates that the protease peptide and the heterologous protein are fused in-frame. The heterologous protein can be fused to the N-terminus or C-terminus of the protease peptide.

In some uses, the fusion protein does not affect the activity of the protease peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant protease peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A protease peptide-encoding nucleic acid can be cloned into such an expression vector such that the fusion moiety is linked in-frame to the protease peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the protease peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the protease peptides of the present invention as well as being encoded by the same genetic locus as the protease peptide provided herein. As indicated by the data presented in FIG. 3, the map position was determined to be on chromosome 1 by ePCR.

Allelic variants of a protease peptide can readily be identified as being a human protein having a high degree (significant) of sequence homology/identity to at least a portion of the protease peptide as well as being encoded by the same genetic locus as the protease peptide provided herein. Genetic locus can readily be determined based on the genomic information provided in FIG. 3, such as the genomic sequence mapped to the reference human. As indicated by the data presented in FIG. 3, the map position was determined to be on chromosome 1 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a protease peptide encoding nucleic acid molecule under stringent conditions as more fully described below.

FIG. 3 provides information on SNPs that have been found in the gene encoding the protease protein of the present invention. SNPs were identified at 7 different nucleotide positions in introns and regions 5' and 3' of the ORF. Such SNPs in introns and outside the ORF may affect control/regulatory elements.

Paralogs of a protease peptide can readily be identified as having some degree of significant sequence homology/identity to at least a portion of the protease peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a protease peptide encoding nucleic acid molecule under moderate to stringent conditions as more fully described below.

Orthologs of a protease peptide can readily be identified as having some degree of significant sequence homology/identity to at least a portion of the protease peptide as well as being encoded by a gene from another organism. Preferred orthologs will be isolated from mammals, preferably primates, for the development of human therapeutic targets and agents. Such orthologs will be encoded by a nucleic acid sequence that will hybridize to a protease peptide encoding nucleic acid molecule under moderate to stringent conditions, as more fully described below, depending on the degree of relatedness of the two organisms yielding the proteins. As indicated by the data presented in FIG. 3, the map position was determined to be on chromosome 1 by ePCR.

FIG. 3 provides information on SNPs that have been found in the gene encoding the protease protein of the present invention. SNPs were identified at 7 different nucleotide positions in introns and regions 5' and 3' of the ORF. Such SNPs in introns and outside the ORF may affect control/regulatory elements.

Non-naturally occurring variants of the protease peptides of the present invention can readily be generated using recombinant techniques. Such variants include, but are not limited to deletions, additions and substitutions in the amino acid sequence of the protease peptide. For example, one class of substitutions are conserved amino acid substitution. Such substitutions are those that substitute a given amino acid in a protease peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant protease peptides can be fully functional or can lack function in one or more activities, e.g. ability to bind substrate, ability to cleave substrate, ability to participate in a signaling pathway, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as protease activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the protease peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a protease peptide. Such fragments can be chosen based on the ability to retain one or more of the biological activities of the protease peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the protease peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in protease peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al (*Meth. Enzymol.* 182: 626–646 (1990)) and Rattan et al. (*Ann. N.Y. Acad. Sci.* 663:48–62 (1992)).

Accordingly, the protease peptides of the present invention also encompass derivatives or analogs in which a substituted amino acid residue is not one encoded by the genetic code, in which a substituent group is included, in which the mature protease peptide is fused with another compound, such as a compound to increase the half-life of the protease peptide (for example, polyethylene glycol), or in which the additional amino acids are fused to the mature protease peptide, such as a leader or secretory sequence or a sequence for purification of the mature protease peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a protease-effector protein interaction or protease-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Utility_Utility

The potential uses of the peptides of the present invention are based primarily on the source of the protein as well as the class/action of the protein. For example, proteases isolated from humans and their human/mammalian orthologs serve as targets for identifying agents for use in mammalian therapeutic applications, e.g. a human drug, particularly in modulating a biological or pathological response in a cell or tissue that expresses the protease. Experimental data as provided in FIG. 1 indicates that protease proteins of the present invention are expressed in the placenta, lung, ovary, colon, kidney, thyroid gland, prostate, eye detected by a virtual northern blot. In addition, PCR-based tissue screening panel indicates expression in leucocyte. A large percentage of pharmaceutical agents are being developed that modulate the activity of protease proteins, particularly members of the metalloprotease subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the placenta, lung, ovary, colon, kidney, thyroid gland, prostate, eye and leucocyte. Such uses can readily be determined using the information provided herein, that which is known in the art, and routine experimentation.

The proteins of the present invention (including variants and fragments that may have been disclosed prior to the present invention) are useful for biological assays related to proteases that are related to members of the metalloprotease subfamily. Such assays involve any of the known protease functions or activities or properties useful for diagnosis and treatment of protease-related conditions that are specific for the subfamily of proteases that the one of the present invention belongs to, particularly in cells and tissues that express the protease. Experimental data as provided in FIG. 1 indicates that protease proteins of the present invention are expressed in the placenta, lung, ovary, colon, kidney, thyroid gland, prostate, eye detected by a virtual northern blot. In addition, PCR-based tissue screening panel indicates expression in leucocyte.

The proteins of the present invention are also useful in drug screening assays, in cell-based or cell-free systems. Cell-based systems can be native, i.e., cells that normally express the protease, as a biopsy or expanded in cell culture. Experimental data as provided in FIG. 1 indicates expression in the placenta, lung, ovary, colon, kidney, thyroid gland, prostate, eye and leucocyte. In an alternate embodiment, cell-based assays involve recombinant host cells expressing the protease protein.

The polypeptides can be used to identify compounds that modulate protease activity of the protein in its natural state or an altered form that causes a specific disease or pathology associated with the protease. Both the proteases of the present invention and appropriate variants and fragments can be used in high-throughput screens to assay candidate compounds for the ability to bind to the protease. These compounds can be further screened against a functional protease to determine the effect of the compound on the protease activity. Further, these compounds can be tested in animal or invertebrate systems to determine activity/effectiveness. Compounds can be identified that activate (agonist) or inactivate (antagonist) the protease to a desired degree.

Further, the proteins of the present invention can be used to screen a compound for the ability to stimulate or inhibit interaction between the protease protein and a molecule that normally interacts with the protease protein, e.g. a substrate or a component of the signal pathway that the protease protein normally interacts (for example, a protease). Such assays typically include the steps of combining the protease protein with a candidate compound under conditions that allow the protease protein, or fragment, to interact with the target molecule, and to detect the formation of a complex between the protein and the target or to detect the biochemical consequence of the interaction with the protease protein and the target, such as any of the associated effects of signal transduction such as protein cleavage, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant proteases or appropriate fragments containing mutations that affect protease function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) protease activity. The assays typically involve an assay of events in the signal transduction pathway that indicate protease activity. Thus, the cleavage of a substrate, inactivation/activation of a protein, a change in the expression of genes that are up- or down-regulated in response to the protease protein dependent signal cascade can be assayed.

Any of the biological or biochemical functions mediated by the protease can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the protease can be assayed. Experimental data as provided in FIG. 1 indicates that protease proteins of the present invention are expressed in the placenta, lung, ovary, colon, kidney, thyroid gland, prostate, eye detected by a virtual northern blot. In addition, PCR-based tissue screening panel indicates expression in leucocyte.

Binding and/or activating compounds can also be screened by using chimeric protease proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native protease. Accordingly, a different set of signal transduction components is available as an end-point assay for activation. This allows for assays to be performed in other than the specific host cell from which the protease is derived.

The proteins of the present invention are also useful in competition binding assays in methods designed to discover compounds that interact with the protease (e.g. binding partners and/or ligands). Thus, a compound is exposed to a protease polypeptide under conditions that allow the compound to bind or to otherwise interact with the polypeptide. Soluble protease polypeptide is also added to the mixture. If the test compound interacts with the soluble protease polypeptide, it decreases the amount of complex formed or activity from the protease target. This type of assay is particularly useful in cases in which compounds are sought that interact with specific regions of the protease. Thus, the soluble polypeptide that competes with the target protease region is designed to contain peptide sequences corresponding to the region of interest.

To perform cell free drug screening assays, it is sometimes desirable to immobilize either the protease protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protease-binding protein and a candidate compound are incubated in the protease protein-presenting wells and the amount of complex trapped in the well can be quantitated. Methods for detecting such complexes, in addition to those described above for the GST-immobilized complexes, include immunodetection of complexes using antibodies reactive with the protease protein target molecule, or which are reactive with protease protein and compete with the target molecule, as well as enzyme-linked assays which rely on detecting an enzymatic activity associated with the target molecule.

Agents that modulate one of the proteases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of protease protein activity identified according to these drug screening assays can be used to treat a subject with a disorder mediated by the protease pathway, by treating cells or tissues that express the protease. Experimental data as provided in FIG. 1 indicates expression in the placenta, lung, ovary, colon, kidney, thyroid gland, prostate, eye and leucocyte. These methods of treatment include the steps of administering a modulator of protease activity in a pharmaceutical composition to a subject in need of such treatment, the modulator being identified as described herein.

In yet another aspect of the invention, the protease proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the protease and are involved in protease activity. Such protease-binding proteins are also likely to be involved in the propagation of signals by the protease proteins or protease targets as, for example, downstream elements of a protease-mediated signaling pathway. Alternatively, such protease-binding proteins are likely to be protease inhibitors.

The two-hybrid system is based on the modular nature of most transcription factors, which consist of separable DNA-binding and activation domains. Briefly, the assay utilizes two different DNA constructs. In one construct, the gene that codes for a protease protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a protease-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the protease protein.

This invention further pertains to novel agents identified by the above-described screening assays. Accordingly, it is within the scope of this invention to further use an agent identified as described herein in an appropriate animal model. For example, an agent identified as described herein (e.g., a protease-modulating agent, an antisense protease nucleic acid molecule, a protease-specific antibody, or a protease-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The protease proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the placenta, lung, ovary, colon, kidney, thyroid gland, prostate, eye and leucocyte. The method involves contacting a biological sample with a compound capable of interacting with the protease protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered protease activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protease protein in which one or more of the protease functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and protease activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the placenta, lung, ovary, colon, kidney, thyroid gland, prostate, eye and leucocyte. Accordingly, methods for treatment include the use of the protease protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the protease proteins. Antibodies can be prepared from any region of the peptide as described herein. However, preferred regions will include those involved in function/activity and/or protease/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that protease proteins of the present invention are expressed in the placenta, lung, ovary, colon, kidney, thyroid gland, prostate, eye detected by a virtual northern blot. In addition, PCR-based tissue screening panel indicates expression in leucocyte. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the placenta, lung, ovary, colon, kidney, thyroid gland, prostate, eye and leucocyte. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the placenta, lung, ovary, colon, kidney, thyroid gland, prostate, eye and leucocyte. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the placenta, lung, ovary, colon, kidney, thyroid gland, prostate, eye and leucocyte. Thus, where a specific protein has been correlated with expression in a specific tissue, antibodies that are specific for this protein can be used to identify a tissue type.

The antibodies are also useful for inhibiting protein function, for example, blocking the binding of the protease peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a protease peptide or protein of the present invention (cDNA, transcript and genomic sequence). Such nucleic acid molecules will consist of, consist essentially of, or comprise a nucleotide sequence that encodes one of the protease peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the protease peptide alone, the sequence encoding the mature peptide and additional coding sequences, such as a leader or secretory sequence (e.g., a pre- pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the protease proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45 C, followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs, including insertion/deletion variants ("indels"), were identified at 7 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 1 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that protease proteins of the present invention are expressed in the placenta, lung, ovary, colon, kidney, thyroid gland, prostate, eye detected by a virtual northern blot. In addition, PCR-based tissue screening panel indicates expression in leucocyte. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in protease protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protease protein, such as by measuring a level of a protease-encoding nucleic acid in a sample of cells from a subject e.g., mRNA or genomic DNA, or determining if a protease gene has been mutated. Experimental data as provided in FIG. 1 indicates that protease proteins of the present invention are expressed in the placenta, lung, ovary, colon, kidney, thyroid gland, prostate, eye detected by a virtual northern blot. In addition, PCR-based tissue screening panel indicates expression in leucocyte.

Nucleic acid expression assays are useful for drug screening to identify compounds that modulate protease nucleic acid expression.

The invention thus provides a method for identifying a compound that can be used to treat a disorder associated with nucleic acid expression of the protease gene, particularly biological and pathological processes that are mediated by the protease in cells and tissues that express it. Experimental data as provided in FIG. 1 indicates expression in the placenta, lung, ovary, colon, kidney, thyroid gland, prostate, eye and leucocyte. The method typically includes assaying the ability of the compound to modulate the expression of the protease nucleic acid and thus identifying a compound that can be used to treat a disorder characterized by undesired protease nucleic acid expression. The assays can be performed in cell-based and cell-free systems. Cell-based assays include cells naturally expressing the protease nucleic acid or recombinant cells genetically engineered to express specific nucleic acid sequences.

The assay for protease nucleic acid expression can involve direct assay of nucleic acid levels, such as mRNA levels, or on collateral compounds involved in the signal pathway. Further, the expression of genes that are up- or down-regulated in response to the protease protein signal pathway can also be assayed. In this embodiment the regulatory regions of these genes can be operably linked to a reporter gene such as luciferase.

Thus, modulators of protease gene expression can be identified in a method wherein a cell is contacted with a candidate compound and the expression of mRNA determined. The level of expression of protease mRNA in the presence of the candidate compound is compared to the level of expression of protease mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate protease nucleic acid expression in cells and tissues that express the protease. Experimental data as provided in FIG. 1 indicates that protease proteins of the present invention are expressed in the placenta, lung, ovary, colon, kidney, thyroid gland, prostate, eye detected by a virtual northern blot. In addition, PCR-based tissue screening panel indicates expression in leucocyte. Modulation includes both up-regulation (i.e. activation or agonization) or down-regulation (suppression or antagonization) or nucleic acid expression.

Alternatively, a modulator for protease nucleic acid expression can be a small molecule or drug identified using the screening assays described herein as long as the drug or small molecule inhibits the protease nucleic acid expression in the cells and tissues that express the protein. Experimental data as provided in FIG. 1 indicates expression in the placenta, lung, ovary, colon, kidney, thyroid gland, prostate, eye and leucocyte.

The nucleic acid molecules are also useful for monitoring the effectiveness of modulating compounds on the expression or activity of the protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in protease nucleic acid expression, and particularly in qualitative changes that lead to pathology. The nucleic acid molecules can be used to detect mutations in protease genes and gene expression products such as mRNA. The nucleic acid molecules can be used as hybridization probes to detect naturally occurring genetic mutations in the protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the protease gene associated with a dysfunction provides a diagnostic tool for an active disease or susceptibility to disease when the disease results from overexpression, underexpression, or altered expression of a protease protein.

Individuals carrying mutations in the protease gene can be detected at the nucleic acid level by a variety of techniques. FIG. 3 provides information on SNPs that have been found in the gene encoding the protease protein of the present invention. SNPs were identified at 7 different nucleotide positions in introns and regions 5' and 3' of the ORF. Such SNPs in introns and outside the ORF may affect control/regulatory elements. As indicated by the data presented in FIG. 3, the map position was determined to be on chromosome 1 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., Science 241:1077–1080 (1988); and Nakazawa et al., PNAS 91:360–364 (1994)), the latter of which can be particularly useful for detecting point mutations in the gene (see Abravaya et al., Nucleic Acids Res. 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant protease gene and a wild-type gene can be determined by direct DNA sequencing. A variety of automated sequencing procedures can be utilized when performing the diagnostic assays (Naeve, C. W., (1995) Biotechniques 19:448), including sequencing by mass spectrometry (see, e.g., PCT International Publication No. WO 94/16101; Cohen et al., Adv. Chromatogr. 36:127–162 (1996); and Griffin et al., Appl. Biochem. Biotechnol. 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al, Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the protease gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control protease gene expression in cells, tissues, and organisms. A DNA antisense nucleic acid molecule is designed to be complementary to a region of the gene involved in transcription, preventing transcription and hence production of protease protein. An antisense RNA or DNA nucleic acid molecule would hybridize to the mRNA and thus block translation of mRNA into protease protein. FIG. 3 provides information on SNPs that have been found in the gene encoding the protease protein of the present invention. SNPs were identified at 7 different nucleotide positions in introns and regions 5' and 3' of the ORF. Such SNPs in introns and outside the ORF may affect control/regulatory elements.

Alternatively, a class of antisense molecules can be used to inactivate mRNA in order to decrease expression of protease nucleic acid. Accordingly, these molecules can treat a disorder characterized by abnormal or undesired protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protease protein, such as substrate binding.

The nucleic acid molecules also provide vectors for gene therapy in patients containing cells that are aberrant in protease gene expression. Thus, recombinant cells, which include the patient's cells that have been engineered ex vivo and returned to the patient, are introduced into an individual where the cells produce the desired protease protein to treat the individual.

The invention also encompasses kits for detecting the presence of a protease nucleic acid in a biological sample. Experimental data as provided in FIG. 1 indicates that protease proteins of the present invention are expressed in the placenta, lung, ovary, colon, kidney, thyroid gland, prostate, eye detected by a virtual northern blot. In addition, PCR-based tissue screening panel indicates expression in leucocyte. For example, the kit can comprise reagents such as a labeled or labelable nucleic acid or agent capable of detecting protease nucleic acid in a biological sample; means for determining the amount of protease nucleic acid in the sample; and means for comparing the amount of protease nucleic acid in the sample with a standard. The compound or agent can be packaged in a suitable container. The kit can further comprise instructions for using the kit to detect protease protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the protease proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the protease gene of the present invention. FIG. 3 provides information on SNPs that have been found in the gene encoding the protease protein of the present invention. SNPs were identified at 7 different nucleotide positions in introns and regions 5' and 3' of the ORF. Such SNPs in introns and outside the ORF may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified protease gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al, *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli, Streptomyces,* and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroprotease. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al, *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual 2nd, ed.,* Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al (*Molecular Cloning: A Laboratory Manual 2nd, ed.,* Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as proteases, appropriate secretion signals are incorporated into the vector. The signal sequence can be endogenous to the peptides or heterologous to these peptides.

Where the peptide is not secreted into the medium, which is typically the case with proteases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a protease protein or peptide that can be further purified to produce desired amounts of protease protein or fragments. Thus, host cells containing expression vectors are useful for peptide production.

Host cells are also useful for conducting cell-based assays involving the protease protein or protease protein fragments, such as those described above as well as other formats known in the art. Thus, a recombinant host cell expressing a native protease protein is useful for assaying compounds that stimulate or inhibit protease protein function.

Host cells are also useful for identifying protease protein mutants in which these functions are affected. If the mutants naturally occur and give rise to a pathology, host cells containing the mutations are useful to assay compounds that have a desired effect on the mutant protease protein (for example, stimulating or inhibiting function) which may not be indicated by their effect on the native protease protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a protease protein and identifying and evaluating modulators of protease protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protease protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the protease protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/toxP recombinase system of bacteriophage P1. For a description of the cre/loxP recombinase system, see, e.g., Lakso et al *PNAS* 89:6232–6236 (1992). Another example of a recombinase system is the FLP recombinase system of *S. cerevisiae* (O'Gorman et al *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, protease protein activity/activation, and signal transduction, may not be evident from in vitro cell-free or cell-based assays. Accordingly, it is useful to provide non-human transgenic animals to assay in vivo protease protein function, including substrate interaction, the effect of specific mutant protease proteins on protease protein function and substrate interaction, and the effect of chimeric protease proteins. It is also possible to assess the effect of null mutations, that is mutations that substantially or completely eliminate one or more protease protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes an amino acid sequence shown in SEQ ID NO:2;
   (b) a nucleic acid molecule consisting of the nucleic acid sequence of SEQ ID No: 1;
   (c) a nucleic acid molecule consisting of the nucleic acid sequence of SEQ ID No: 3; and
   (d) a nucleotide sequence that is completely complementary to a nucleotide sequence of (a)–(c).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering the peptide from the host cell culture.

5. An isolated polynucleotide consisting of a nucleotide sequence set forth in SEQ ID NO:1.

6. An isolated polynucleotide consisting of a nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO: 2 may be expressed by a cell transformed with said vector.

9. A vector according to claim 8, wherein said isolated nucleic acid molecule is operatively linked to a promoter sequence.

* * * * *

SEQUENCE LISTING

<160> NUMBER OF SEQ ID NOS: 4

<210> SEQ ID NO 1
<211> LENGTH: 2968
<212> TYPE: DNA
<213> ORGANISM: Human

<400> SEQUENCE: 1

| | | | | | |
|---|---|---|---|---|---|
| cgacctggcc | gccggccgct | cctccgcgcg | ctgttccgca | cttgctgccc | tcgcccggcc | 60 |
| cggagcgccg | ctgccatgcg | gctggcgctg | ctctgggccc | tggggctcct | gggcgcgggc | 120 |
| agccctctgc | cttcctggcc | gctcccaaat | atagccctgc | tgtcgattcc | ctcagtactg | 180 |
| tcttggggtg | tcctgggacc | tgcaggtggc | actgaggagc | agcaggcaga | gtcagagaag | 240 |
| gccccgaggg | agcccttgga | gcccaggtc | cttcaggacg | atctcccaat | tagcctcaaa | 300 |
| aaggtgcttc | agaccagtct | gcctgagccc | ctgaggatca | agttggagct | ggacggtgac | 360 |
| agtcatatcc | tggagctgct | acagaatagg | gagttggtcc | caggccgccc | aaccctggtg | 420 |
| tggtaccagc | ccgatggcac | tcgggtggtc | agtgagggac | acactttgga | gaactgctgc | 480 |
| taccagggaa | gagtgcgggg | atatgcaggc | tcctgggtgt | ccatctgcac | ctgctctggg | 540 |
| ctcagaggct | tggtggtcct | gacccagag | agaagctata | ccctggagca | ggggcctggg | 600 |
| gaccttcagg | gtcctccat | tatttcgcga | atccaagatc | tccacctgcc | aggccacacc | 660 |
| tgtgccctga | gctggcggga | atctgtacac | actcagacgc | caccagagca | cccctggga | 720 |
| cagcgccaca | ttcgccggag | gcgggatgtg | gtaacagaga | ccaagactgt | ggagttggtg | 780 |
| attgtggctg | atcactcgga | ggcccagaaa | taccgggact | tccagcacct | gctaaaccgc | 840 |
| acactggaag | tggccctctt | gctggacaca | ttcttccgc | ccctgaatgt | acgagtggca | 900 |
| ctagtgggcc | tggaggcctg | gacccagcgt | gacctggtgg | agatcagccc | aaacccagct | 960 |
| gtcaccctcg | aaaacttcct | ccactggcgc | agggcacatt | tgctgcctcg | attgccccat | 1020 |
| gacagtgccc | agctggtgac | tggtacttca | ttctctgggc | ctacggtggg | catggccatt | 1080 |
| cagaactcca | tctgttctcc | tgacttctca | ggaggtgtga | acatggacca | ctccaccagc | 1140 |
| atcctgggag | tcgcctcctc | catagcccat | gagttgggcc | acagcctggg | cctgaccat | 1200 |
| gatttgcctg | ggaatagctg | cccctgtcca | ggtccagccc | cagccaagac | ctgcatcatg | 1260 |
| gaggcctcca | cagacttcct | accaggcctg | aacttcagca | actgcagccg | acgggccctg | 1320 |
| gagaaagccc | tcctggatgg | aatgggcagc | tgcctcttcg | aacggctgcc | tagcctaccc | 1380 |
| cctatgctgc | ctttctgcgg | aaatatgttt | gtggagccgg | gcgagcagtg | tgactgtggc | 1440 |
| ttcctggatg | actgcgtcga | tccctgctgt | gattctttga | cctgccagct | gaggccaggt | 1500 |
| gcacagtgtg | catctgacgg | accctgttgt | caaaattgcc | agctgcgccc | gtctggctgg | 1560 |
| cagtgtcgtc | ctaccagagg | ggattgtgac | ttgcctgaat | tctgcccagg | agacagctcc | 1620 |
| cagtgtcccc | ctgatgtcag | cctagggat | ggcgagccct | cgctggcgg | gcaagctgtg | 1680 |
| tgcatgcacg | ggcgttgtgc | ctcctatgcc | cagcagtgcc | agtcactttg | ggacctgga | 1740 |
| gcccagcccg | ctgcgccact | ttgcctccag | acagctaata | tcggggaaa | tgcttttggg | 1800 |
| agctgtgggc | gcaaccccag | tggcagttat | gtgtcctgca | ccctagaga | tgccatttgt | 1860 |
| gggcagctcc | agtgccagac | aggtaggacc | cagcctctgc | tgggctccat | ccggatcta | 1920 |
| ctctgggaga | caatagatgt | gaatgggact | gagctgaact | gcagctgggt | gcacctggac | 1980 |
| ctgggcagtg | atgtggcccca | gcccctcctg | actctgcctg | gcacagcctg | tggccctggc | 2040 |

-continued

```
ctggtgtgta tagaccatcg atgccagcgt gtggatctcc tgggggcaca ggaatgtcga      2100
agcaaatgcc atggacatgg ggtctgtgac agcaacaggc actgctactg tgaggagggc      2160
tgggcacccc ctgactgcac cactcagctc aaagcaacca gctccctgac cacagggctg      2220
ctcctcagcc tcctggtctt attggtcctg gtgatgcttg gtgccagcta ctggtaccgt      2280
gcccgcctgc accagcgact ctgccagctc aagggaccca cctgccagta cagggcagcc      2340
caatctggtc cctctgaacg gccaggacct ccgcagaggg ccctgctggc acgaggcact      2400
aaggctagtg ctctcagctt cccggccccc ccttccaggc cgctgccgcc tgaccctgtg      2460
tccaagagac tccagtctca ggggccagcc aagcccccac ccccaaggaa gccactgcct      2520 gccgacccc agggccggtg cccatcgggt gacctgcccg gccagggc tggaatcccg          2580 cccctagtgg taccctccag accagcgcca ccgcctccga cagtgtcctc gctctacctc      2640
tgacctctcc ggaggttccg ctgcctccaa gccggactta gggcttcaag aggcgggcgt      2700
gccctctgga gtcccctacc atgactgaag gcgccagaga ctggcggtgt cttaagactc      2760
cgggcaccgc cacgcgctgt caagcaacac tctgcggacc tgccggcgta gttgcagcgg      2820
gggcttgggg aggggctggg ggttggacgg gattgaggaa ggtccgcaca gcctgtctct      2880
gctcagttgc aataaacgtg acatcttgga aaaaaaaaa aaaaaaaaaa aaaaaaaaaa      2940
aaaaaaaaaa aaaaaaaaaa aaaaaaaa                                         2968
```

<210> SEQ ID NO 2
<211> LENGTH: 855
<212> TYPE: PRT
<213> ORGANISM: Human

<400> SEQUENCE: 2

```
Met Arg Leu Ala Leu Leu Trp Ala Leu Gly Leu Leu Gly Ala Gly Ser
 1               5                  10                  15

Pro Leu Pro Ser Trp Pro Leu Pro Asn Ile Ala Leu Leu Ser Ile Pro
                20                  25                  30

Ser Val Leu Ser Trp Gly Val Leu Gly Pro Ala Gly Gly Thr Glu Glu
            35                  40                  45

Gln Gln Ala Glu Ser Glu Lys Ala Pro Arg Glu Pro Leu Glu Pro Gln
        50                  55                  60

Val Leu Gln Asp Asp Leu Pro Ile Ser Leu Lys Lys Val Leu Gln Thr
 65                  70                  75                  80

Ser Leu Pro Glu Pro Leu Arg Ile Lys Leu Glu Leu Asp Gly Asp Ser
                85                  90                  95

His Ile Leu Glu Leu Leu Gln Asn Arg Glu Leu Val Pro Gly Arg Pro
                100                 105                 110

Thr Leu Val Trp Tyr Gln Pro Asp Gly Thr Arg Val Val Ser Glu Gly
            115                 120                 125

His Thr Leu Glu Asn Cys Cys Tyr Gln Gly Arg Val Arg Gly Tyr Ala
        130                 135                 140

Gly Ser Trp Val Ser Ile Cys Thr Cys Ser Gly Leu Arg Gly Leu Val
145                 150                 155                 160

Val Leu Thr Pro Glu Arg Ser Tyr Thr Leu Glu Gln Gly Pro Gly Asp
                165                 170                 175

Leu Gln Gly Pro Pro Ile Ile Ser Arg Ile Gln Asp Leu His Leu Pro
                180                 185                 190

Gly His Thr Cys Ala Leu Ser Trp Arg Glu Ser Val His Thr Gln Thr
            195                 200                 205
```

-continued

```
Pro Pro Glu His Pro Leu Gly Gln Arg His Ile Arg Arg Arg Asp
    210                 215                 220
Val Val Thr Glu Thr Lys Thr Val Glu Leu Val Ile Val Ala Asp His
225                 230                 235                 240
Ser Glu Ala Gln Lys Tyr Arg Asp Phe Gln His Leu Leu Asn Arg Thr
                245                 250                 255
Leu Glu Val Ala Leu Leu Leu Asp Thr Phe Phe Arg Pro Leu Asn Val
                260                 265                 270
Arg Val Ala Leu Val Gly Leu Glu Ala Trp Thr Gln Arg Asp Leu Val
                275                 280                 285
Glu Ile Ser Pro Asn Pro Ala Val Thr Leu Glu Asn Phe Leu His Trp
    290                 295                 300
Arg Arg Ala His Leu Leu Pro Arg Leu Pro His Asp Ser Ala Gln Leu
305                 310                 315                 320
Val Thr Gly Thr Ser Phe Ser Gly Pro Thr Val Gly Met Ala Ile Gln
                325                 330                 335
Asn Ser Ile Cys Ser Pro Asp Phe Ser Gly Gly Val Asn Met Asp His
                340                 345                 350
Ser Thr Ser Ile Leu Gly Val Ala Ser Ser Ile Ala His Glu Leu Gly
            355                 360                 365
His Ser Leu Gly Leu Asp His Asp Leu Pro Gly Asn Ser Cys Pro Cys
    370                 375                 380
Pro Gly Pro Ala Pro Ala Lys Thr Cys Ile Met Glu Ala Ser Thr Asp
385                 390                 395                 400
Phe Leu Pro Gly Leu Asn Phe Ser Asn Cys Ser Arg Arg Ala Leu Glu
                405                 410                 415
Lys Ala Leu Leu Asp Gly Met Gly Ser Cys Leu Phe Glu Arg Leu Pro
                420                 425                 430
Ser Leu Pro Pro Met Ala Ala Phe Cys Gly Asn Met Phe Val Glu Pro
            435                 440                 445
Gly Glu Gln Cys Asp Cys Gly Phe Leu Asp Asp Cys Val Asp Pro Cys
    450                 455                 460
Cys Asp Ser Leu Thr Cys Gln Leu Arg Pro Gly Ala Gln Cys Ala Ser
465                 470                 475                 480
Asp Gly Pro Cys Cys Gln Asn Cys Gln Leu Arg Pro Ser Gly Trp Gln
                485                 490                 495
Cys Arg Pro Thr Arg Gly Asp Cys Asp Leu Pro Glu Phe Cys Pro Gly
                500                 505                 510
Asp Ser Ser Gln Cys Pro Pro Asp Val Ser Leu Gly Asp Gly Glu Pro
            515                 520                 525
Cys Ala Gly Gly Gln Ala Val Cys Met His Gly Arg Cys Ala Ser Tyr
    530                 535                 540
Ala Gln Gln Cys Gln Ser Leu Trp Gly Pro Gly Ala Gln Pro Ala Ala
545                 550                 555                 560
Pro Leu Cys Leu Gln Thr Ala Asn Thr Arg Gly Asn Ala Phe Gly Ser
                565                 570                 575
Cys Gly Arg Asn Pro Ser Gly Ser Tyr Val Ser Cys Thr Pro Arg Asp
                580                 585                 590
Ala Ile Cys Gly Gln Leu Gln Cys Gln Thr Gly Arg Thr Gln Pro Leu
            595                 600                 605
Leu Gly Ser Ile Arg Asp Leu Leu Trp Glu Thr Ile Asp Val Asn Gly
    610                 615                 620
```

```
Thr Glu Leu Asn Cys Ser Trp Val His Leu Asp Leu Gly Ser Asp Val
625                 630                 635                 640

Ala Gln Pro Leu Leu Thr Leu Pro Gly Thr Ala Cys Gly Pro Gly Leu
            645                 650                 655

Val Cys Ile Asp His Arg Cys Gln Arg Val Asp Leu Leu Gly Ala Gln
                660                 665                 670

Glu Cys Arg Ser Lys Cys His Gly His Gly Val Cys Asp Ser Asn Arg
            675                 680                 685

His Cys Tyr Cys Glu Glu Gly Trp Ala Pro Pro Asp Cys Thr Thr Gln
690                 695                 700

Leu Lys Ala Thr Ser Ser Leu Thr Thr Gly Leu Leu Leu Ser Leu Leu
705                 710                 715                 720

Val Leu Leu Val Leu Val Met Leu Gly Ala Ser Tyr Trp Tyr Arg Ala
                725                 730                 735

Arg Leu His Gln Arg Leu Cys Gln Leu Lys Gly Pro Thr Cys Gln Tyr
            740                 745                 750

Arg Ala Ala Gln Ser Gly Pro Ser Glu Arg Pro Gly Pro Pro Gln Arg
            755                 760                 765

Ala Leu Leu Ala Arg Gly Thr Lys Ala Ser Ala Leu Ser Phe Pro Ala
770                 775                 780

Pro Pro Ser Arg Pro Leu Pro Pro Asp Pro Val Ser Lys Arg Leu Gln
785                 790                 795                 800

Ser Gln Gly Pro Ala Lys Pro Pro Pro Arg Lys Pro Leu Pro Ala
                805                 810                 815

Asp Pro Gln Gly Arg Cys Pro Ser Gly Asp Leu Pro Gly Pro Gly Ala
                820                 825                 830

Gly Ile Pro Pro Leu Val Val Pro Ser Arg Pro Ala Pro Pro Pro Pro
            835                 840                 845

Thr Val Ser Ser Leu Tyr Leu
    850                 855

<210> SEQ ID NO 3
<211> LENGTH: 17138
<212> TYPE: DNA
<213> ORGANISM: Human
<220> FEATURE:
<221> NAME/KEY: misc_feature
<222> LOCATION: (1)...(17138)
<223> OTHER INFORMATION: n = A,T,C or G

<400> SEQUENCE: 3
ttgggtgacc ctgggcagtg atcacatctc caagcatcag ttttctcacc tgaaaaaaag      60
gagatgataa taacactatc tgccttacat gacaattgaa ttgaattttt ttttttttt     120 tgagactaag tctcactctg tcgcccaggc tggagtgcag tggcgtgatc ttggctcact    180
gcaacctcca cctccccagt tcaagcgatt ctcgtgcctc agcttcccga gtagctggga    240
ttacaggcac acactaccac gcccggctaa tttagaattg aaataattta tgtacagtat    300
cttagtacag gacctgacat tataaacaat gagtggcagc cattcttatt taatcagtcc    360
taacaaagtt cataaaagtg agactgtgtt tgcttagctt tttccctagg gcctggatac    420
ccccagcccc catgacacac aatagggggcc aatgaatgt gttgtgaaaa atgaaaaac    480 aaaaaacaaa aagaacatg ctgggattcc ttgacagggt cgtgaagcaa actgaatgtg    540
aatgcacaga tggaaatgtg ccagacagtc attccaagca gaatgtgcaa agactcagtc    600
cacagggaat gcgaagtgcc aggctagtc tcaggagaaa ctggctcaga agagacagct    660
```

-continued

| | |
|---|---|
| ctcagggagg gctaaagtag gaaagaggct agaaagggac caggtgaggg aaggctctga | 720 |
| aggccaagcc caagagttct gcctgtctgg caggcagcag ggcctctgga gtttcttggg | 780 |
| caaagagtgg ctgcttcctg gtaaggtgg cctgtggaaa atccctgaca actgtgtaga | 840 |
| gacatgtcgt gagggatggc aggagcata gtgaactagg tttgtggttt ggaatcaggg | 900 |
| cccctggggt ccagccaagt tggattgttt actatctgtg tgactttgag agtcacttca | 960 |
| cctttctcaa ctgtaaagtg gggatagcaa cagtgatagt cgatctggcc tgctcacttc | 1020 |
| tcagcctcac tgtgagaacc aaataagatg atttacagga aagtgcaaat gagagttgtg | 1080 |
| gctgatatcc gcttggagag agcctggagg gtgcatcctc ccattctcca tcacagagtt | 1140 |
| ggggagggag gcaccctcgc cctccagggg tttcctttgt ccaacccagc ctcctccaac | 1200 |
| acgcgggaat tgtcaggcct ggcgacttca gacaggaaac gctgtccagt tccccttctt | 1260 |
| tcccgcctcg ctcccgggct ggcgctaacg cccacctccc aacagcgcca cccgctggcg | 1320 |
| gatatcctgc accgcggctg cccgctcctg cgccgctggc tgtgccggcg ctgcgtggtg | 1380 |
| tgccaggcac ccgagacgcc cgagtcctac gtgtgccgga cgctggactg cgaggccgtg | 1440 |
| tactgctggt cgtgctggga cgacatgcgg cagcggtgcc cggtctgcac gccccgcgaa | 1500 |
| gagctctctt cctccgcctt tagtgacagc aacgacgaca ctgcctacgc ggggtgaaga | 1560 |
| ggcgtcctgc tcgctcttcc gcaccgtcct tcccggttaa taaaatgccc tgtacgcttc | 1620 |
| acgtgggtcg gggactgggg tgagccgcgc actgcctcgc ctgcagtcgg gaaagcctgc | 1680 |
| ccgcccgacc tctccgagcc aggccgcgca caggaggcag ggaggccgcg aagctactag | 1740 |
| ggaggggtcc ggacctggcg ccgggtgaag gcgcgccgcc caagccggtc ggaccgggca | 1800 |
| ccggctccca ctccgcacag ttgcgcggaa gcggtagcgc tgagcagcgc gggcgtagtg | 1860 |
| ggcggtgtcc ccgctcccga ggcacccggc gcgcagcggg gcgggcttg ccggggcgg | 1920 |
| agcttggctt ggggccgggt gggaggggc gggccgggc gggcctggt ggccgcgcgg | 1980 |
| cgctgctggg ttctccgagg cgacctggcc gccggccgct cctccgcgcg ctgttccgca | 2040 |
| cttgctgccc tcgcccggcc cggagcgcgc ctgccatgcg gctggcgctg ctctgggccc | 2100 |
| tggggctcct gggcgcgggc agccctctgc cttcctggcc gctcccaaat ataggtgagt | 2160 |
| cctccgcctg gagtgggtcg gggggcggac tgggagggag gtgcaggaaa gtcggaaggc | 2220 |
| attagggtaa tggggccgga cggagaccct gggagagccc agccagagcg cggcccgccc | 2280 |
| tggtccgctg tcctgggcct agggcccggt gacttggcga tggggtgaaa agagaaggag | 2340 |
| gggggatgcc ggcgccccct gcctcctgcc tggtcatcct ctgcgcggtc cctgcggaca | 2400 |
| ctttcaggct caggtaccag gtaccgaggg gcctgtccag cgccacttca agatcgtgat | 2460 |
| gagagggtcg ctgctcccca ggactggcat cttcgctgct ctgggccta gctaaccgtt | 2520 |
| ccacccggtg ccaggcgct gagcgggcat ggcttgtagg gtttagtgaa gaggattctc | 2580 |
| tctagcctct attccaggcc tggggccgcc aggcactcct caccctggtg ctgttgccac | 2640 |
| cagtgcctgg ccgagcggga ggggcccgag atgagccagg agaagggaga attggccagg | 2700 |
| aaagaggctg ggacaccaac tcctccttgg aactttcact tcccgctgct gtcttgggcc | 2760 |
| gggaccgaga gggcaggcgc gggtggagtg tccggaggag agaggccat tgtgtgttgg | 2820 |
| gggggtgggg ggtgctcgag gaggaagcag aggctgtagg cagcgggtgt gcctgactgg | 2880 |
| gcatgagggt gtttagggag gtgggggtgt ttgcactgct cacccagaaa tgggcgttcc | 2940 |
| tggcatctcc gatgtgagcg aagggagggg tgagcggca cccggccaca aggcttagct | 3000 |
| cagtctcgag agggggcgtt cctgaagtgg ggggagagtg attgggaggg agtgggaacc | 3060 |

```
gcggagggtc ctgtgagaac ctgggattgg ccggaagggg acaaggaggg ccacaggctg    3120
cgcaagccga aagtctttct tggggacttg tgaatgggtt ggtgggtgga aagccataaa    3180
ttagagagac accctctcct tccagtattc ttctttaagt ctcagcatgc aatgtggaag    3240
cccctcaggt acctaagggt cttgatgggc tgggagctgg tggatctgag ggcacctgtc    3300
acccccagcc ctgctgtcga ttccctcagt actgtcttgg ggtgtcctgg gacctgcagg    3360
tggcactgag gagcagcagg cagagtcaga gaaggccccg agggagccct tggagcccca    3420
ggtccttcag gacgatctcc caattagcct caaaaaggtg cttcaggtga gctctcactc    3480
ccctctaata aataaacgaa tccacacacg ccccggtata gccaggtgtc tcaaagccaa    3540
agcttggctg aggagctggt gggtagagct cactgtagtg ggtctatccc aggcccagct    3600
gcctctccca ccacacccca gcacctggct tcacttatct ccctctccct ctgcacacac    3660
gtgtatctgt ctgcctcagc cccacccaac ccatccatct ccactgggga aattgtgaag    3720
ccaaacttgc tttcttcatc tcatgttgtc ggttttctca gtgggggat ttggaaagag     3780
tcaggacctt accaaacccc ccccccccac cccattctaa agctgagtca gaggaagggc    3840
tggggcttgt gctgggtcct acacggtgct tcctctctgg gcaggaagcc gagaagggt     3900
ggctcagata ccttccttga cctccgcaca caaccccca gaacaatgct ccaggccagg     3960
cagggtttcc tggcccctcc cctgggatcc cccaccagt gatctaattg ctggtgctct     4020
tctgtgggcc tgaggttttc tggttagaga ggctgggagt tgtggacagg tctagggagg    4080
tgacctgccc tctggtgccc acagaccagt ctgcctgagc ccctgaggat caagttggag    4140
ctggacggtg acagtcatat cctggagctg ctacagaata ggtaatagtg atggtggcaa    4200
taacagtgac cacatggcca acaacttgta tagcatttat tatgtgccag gtactaagtg    4260
cttgtgctca tttaatcctc ataacagccc tataagggat atactatcat gtattattgt    4320
cctcactta tacatgagga agtcaaggca cagagagatt aaataacttg ccccaggtca     4380
cacagctagt atgtggtgaa aaccagattg gaattcaaat aaactaacag agtcagtggc    4440
ccaaccagta tactttgctg ccccggggtc aggagtggaa aagttggctg cggggggttgc   4500
ctggtcccca gccccacaac caccttcaag cctctgcttg tcaatgcacc gaccctggga    4560
agtggcttta gcactgcctt cttttcttc acttcacagg ggagttggtc ccatgtccgc     4620
cccgacccttt ggggtccggc tntccctct ccccccttcg gcgccgcccc ttccttttc     4680
tttcttcccc tccgctttcg tccttttgcc tccccgtgc cgttgcgcgt tccttcttcc    4740
ccgttccctc tccctctttt tgttccctcc cgttcttttc tccccgcgt tctttcctcc     4800
tccttttcgg tccgccctcg ccttcctccc ttccccttct gccttcgcc ntttctccct    4860
ctcgttcttc ctcggtgtcg cgtcgtcccg gctcggcctt tccccgcttc ctcccgctcg    4920
ccgttttttt cccccgctg tcttcccgtg ttccccttcg cttctcctct tccctttcgt    4980
tcggtcgttt tctcgttcca ttcccgcctc cccgtttccg ttccactcct tcttcctcct    5040
ttcccgctcc ccgtttctcc cgaccccaac aacaaataaa nnnnnnnnnn nnnnnnnnnn   5100
nnnnnnnnnn nnnnnnnnnn nnnnnnnnnn nnnnnnnnnn nnnnnnnnnn nnnnnnnnnn   5160
nnnnnnnnnn nnnnnnnnnn nnnnnnnnnn nnnnnnnnnn nnnnnnnnnn nnnnnnnnnn   5220
nnnnnnnnnn nnnnnnnnnn nnnnnnnnnn nnnnnnnnnn nnnnnnnnnn nnnnnnnnnn   5280
nnnnnnnnnn nnnnnnnnnn nnnnnnnnnn nnnnnnnnnn nnnnnnnnnn nnnnnnnnnn   5340
nnnnnnnnnn nnnnnnnnnn nnnnnnnnnn nnnnnnnnnn nnnnnnnnnn nnnnnnnnnn   5400
```

-continued

```
nnnnnnnnnn nnnnnnnnnn nnnnnnnnnn nnnnnnnnnn nnnnnnnnnn nnnnnnnnnn     5460
nnnnnnnnnn nnnnnnnnnn nnnnnnnnnn nnnntcagg aggccgagtg gaagaatcgc      5520
ttgagcccag gtaggcagag gtttcagtgg gccgagatcg agccactaca caccagcctg     5580
ggtgaaagag tgagacctcg tctcaaaaaa taaaataaaa ataaaataaa ataaaatcta     5640
gctgagacag attaggtggt ttgcccgagg ccctacaact aataaatggc ctatccattt     5700
attagttgta tttggctctt catctgtctt atgatcccat ttgcagagag ctctcacttg     5760
gttatagata atacatagtt accaatgatg aagcaatata aacccaattt cctaatttgt     5820
aaaatgaaga taataaaact acttgctgca tagagttgct gggaagatta aataagtcca     5880
tatagatgta aagtgcttaa aactatgcca gacctatggt aagtgacaag agttgttatt     5940 gggatttta aaattattat tattattatt attattattt gagacagagt ctcgctctgt      6000
ctcccaggct ggagtgcagt ggcgtgatct cggctcactg caagctccgc ctcccaggtt     6060
cacgccattc tcttgcctca gcctcccgag tagctgggac tacaggcgcc cgccactaca     6120
cccggctaat gttttgtatt ttttagtaca gacagggttt caccgtgtta tccaggatgg     6180
tctcgatctc ctgacctcat gatccacccg ccttgtcctc ccaaagtgct gagattacag     6240
gcgtgagcca ccgcacccag ctaaattact gttttttaaa aatttgaaaa aaaccactga     6300
gtttggagcc agaaaagcag gggtctactc caaccttcat tatctacttc ctggtcctcc     6360
ttggcaagtt cctgggccct ctggccttca gtggctcatc tgtaaaatgg gctcttcacc     6420
ctcctatttg acccacagag taggagtggc tgcctcttgg tcagcccggc acagctgctg     6480
gctgcgagcg gcaggtttgc ctgataattc ttcttgtcca tagtagaggc gggatgtggt     6540
aacagagacc aagactgtgg agttggtgat tgtggctgat cactcggagg tgagcctgct     6600 ggccctgca catcctcctc cccctgcact gccctgccgc ctttcatgtc acctctcttg      6660
gcctacaggc ccagaaatac cgggacttcc agcacctgct aaaccgcaca ctggaagtgg     6720
ccctcttgct ggacacagtg agtgctggac agggcaaccc ccaccccagg cccctgacca     6780 tggcaaccc tcttctgagc cccagctgtc tttcagttct ccggcccct gaatgtacga      6840 gtggcactag tgggcctgga ggcctggacc cagcgtgacc tggtggagat cagcccaaac     6900
ccagctgtca ccctcgaaaa cttcctccac tggcgcaggg cacatttgct gcctcgattg     6960
ccccatgaca gtgcccagct ggtgacgtaa gggccccaga ctcagccaga gaggccagtc     7020
ctgtcctggc caaattcaca ccccttcagc accctacctc agcccctgaa gctctgacca     7080
ccgtggcttc tggccctgaa ctttagcctc tctgtccac agtggtactt cattctctgg      7140
gcctacggtg ggcatggcca ttcagaactc catctgttct cctgacttct caggaggtgt     7200
gaacatggtg agttatttcc aggtctcctc ctcattccca attcagttcc tcccaagtgt     7260
ggtggcattt atgcactgaa acccccctat aaagttgccc aaccccaaag ctacaggtat     7320
agagggtgga ggtacgtgat gtggccttg ctatcaggga gccctcgctt atggccagct      7380
agtcacagtg tacacagtca tccctgtgc agtcttccca tttcttagag gagggtagga     7440
ggcagctaag gcccaaagaa cagaggtgat ctccctccag tgagggaggg ggacagagct     7500
gagctagaac ccaagtttct gccatccagg cctgggttct cctactttag aagcaattca     7560
ggagggaagc agtgcctgct gagtgcccac gaggtcagac gtggagggaa caggagcaga     7620
gagggtggtc tgggcattgt ggtggaggca ggctgggact ggacctacag tacccctccc     7680
caatgacagg accactccac cagcatcctg ggagtcgcct cctccatagc ccatgagttg     7740
ggccacagcc tgggcctgga ccatgatttg cctgggaata gctgcccctg tccaggtcca     7800
```

-continued

| | |
|---|---|
| gccccagcca agacctgcat catggaggcc tccacagagt aagtagctgc aggatggaga | 7860 |
| gagggtgtgg ggcaggggggc agggannnnn nnnnnnnnnn nnnnnnnnnn tgttagagtt | 7920 |
| accttccttg ccaccctccc cagcttccta ccaggcctga acttcagcaa ctgcagccga | 7980 |
| cgggccctgg agaaagccct cctggatgga atgggcagct gcctcttcga acggctgcct | 8040 |
| agcctacccc ctatggctgc tttctgcgga aatatgtttg tggagccggg cgagcagtgt | 8100 |
| gactgtggct tcctggatgt gagccccttt cccaaagcct cgccccactc acttctgtac | 8160 |
| cctcaccctg gctcattagc cctatcccag cctcctgagc tcttgggttc tgaagggact | 8220 |
| ttccacccct ctcctacttg ccctgtctgt ggggacagca catgggttgt tgggctctag | 8280 |
| ccctcgcttg ctgtgtagct tctggtcttg gcctgtggga ggaggagaga ttggagggag | 8340 |
| gctcacaggc cccacctgct ctgatgcccg gccccgtgc tcctgcccac aggactgcgt | 8400 |
| cgatccctgc tgtgattctt tgacctgcca gctgaggcca ggtgcacagt gtgcatctga | 8460 |
| cggaccctgt tgtcaaaatt gccaggtggg tagagactag actggccacc cggagctcac | 8520 |
| ctgccggggc caaggtggaa aggtcattc tgacccccgg ctggatttgc tcagtgccca | 8580 |
| cactgatgct catccaccct ccacagctgc gcccgtctgg ctggcagtgt cgtcctacca | 8640 |
| gaggggattg tgacttgcct gaattctgcc caggagacac ctcccagtgt cccctgatg | 8700 |
| tcagcctagg ggatggcgag ccctgcgctg gcgggcaagc tgtgtgcatg cacgggcgtt | 8760 |
| gtgcctccta tgcccagcag tgccagtcac tttggggacc tggagcccag cccgctgcgc | 8820 |
| cactttgcct ccagaccgct aatactcggg gaaatgcttt tgggagctgt gggcgcaacc | 8880 |
| ccagtggcag ttatgtgtcc tgcacccta ggtaagtgag gaaacctggc tcctcctttg | 8940 |
| ggtttctgag agccttggcc ctgctcctac taactctgtg tgcccttccc cctcnnnnnn | 9000 |
| nnnnnnnnnn nnnnnnnnnn nnnnnnnnnn nnnnnnnnnn nnnnttacgg catttgtagt | 9060 |
| tactcacact tttgccttca nacagctaat actcgggaa atgcttttgg gagctgtggg | 9120 |
| cgcaaccca gtggcagtta tgtgtcctgc acccctaggt aagtgaggaa acctggctcc | 9180 |
| tcctttgggt ttctgagagc cttggccctg ctcctactaa ctctgtgtgc ccttcccct | 9240 |
| ccccacagag atgccatttg tgggcagctc cagtgccaga caggtaggac ccagcctctg | 9300 |
| ctgggctcca tccgggatct actctgggag acaatagatg tgaatgggac tgagctgaac | 9360 |
| tgcagctggg tgcacctgga cctgggcagt gatgtggccc agcccctcct gactctgcct | 9420 |
| ggcacagcct gtggccctgg cctggtgagc agcctgggtg ggcaagacca ggtgtgagaa | 9480 |
| gggacatttg gaccacaatg aacagagccc agcttcacc attcaccaat gtcaaaggca | 9540 |
| gggactccaa gggaagtcag tttcttactt cagatggagc aaagtcctat caactcacta | 9600 |
| tgccttggtt tccccatctg taaacgcagg gtatggcctc aaccttattg gcctcccagt | 9660 |
| cccattaaag ctttgtggga atctgatcca ggctcttctc tccctgggtc aggtgtgtat | 9720 |
| agaccatcga tgccagcgtg tggatctcct gggggcacag gaatgtcgaa gcaaatgcca | 9780 |
| tggacatggg gtgagctggg atgggggaag tggaagggga gcagagagcc tctagagagg | 9840 |
| aaaaggatac tgggctttgg aaatagacat atctgggttt taatccttgc tctactactt | 9900 |
| cccagttgtg tgacctcggg caggttacta actttgctga gctcagtttc cccacctatc | 9960 |
| aaatggctat aataatagta tccccatcca gggtacatga gatgtgtatg caagcaagta | 10020 |
| gcacagtggg taactaatag tgcttttaaa aannnnnnnn nnnnnnnnnn nnnnnnnnnn | 10080 |
| nnnnnnnnnn nnnnnnnnnn nnnnnnnnnn nnnnnnnnnn nnnnnnnnnn nnnnnnnnnn | 10140 |

-continued

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 10200 |
| nnnnnnnnnn | nnnnnnnnnn | nnnnnnnnnn | nnnnnnnnnn | nnnnnnnnnn | nnnnnnnnnn | 10260 |
| nnnnnnnnnn | nnnnnnnnnn | nnnnnnnnnn | nnnnnnnnnn | nnnnnnnnnn | nnnnnnnnnn | 10320 |
| nnnnnnnnnn | nnnnnnnnnn | nnnnnnnnnn | nnnnnnnnnn | nnnnnnnnnn | nnnnnnnnnn | 10380 |
| nnnnnnnnnn | nnnnnnnnnn | nnnnnnnnnn | nnnnnnnnnn | nnnnnnnnnn | nnnnnnnnnn | 10440 |
| nnnnnnnnnn | nnnnnnnnnn | nnnnnnnnnn | nnnnnnnnnn | nnnnnnnnnn | nnnnnnnnnn | 10500 |
| nnnnnnnnnn | nnnnnnnnnn | nnnnnnnnnn | nnnnnnnnnn | nnnnnnnnnn | nnnnnnnnnn | 10560 |
| nnnnnnnnnn | nnnnnnnnnn | nnnnnnnnnn | nnnnnnnnnn | nnnnnnnnnn | nnnnnnnnnn | 10620 |
| nnnnnnnnnn | nnnnnnnnnn | nnnnnnnnnn | nnnnnnnnnn | nnnnnnnnnn | nnnnnnnnnn | 10680 |
| nnnnnnnnnn | nnnnnnnnnn | nnnnnnnnnn | nnnnnnnnnn | nnnnnnnnnn | nnnnnnnnnn | 10740 |
| nnnnnnnnnn | nnnnnnnnnn | nnnnnnnnnn | nnnnnnnnnn | nnnnnnnnnn | nnnnnnnnnn | 10800 |
| nnnnnnnnnn | nnnnnnnnnn | nnnnnnnnnn | nnnnnnnnnn | nnnnnnnnnn | nnnnnnnnnn | 10860 |
| nnnnnnnnnn | nnnnnnnnnn | nnnnnnnnnn | nnnnnnnnnn | nnnnnnnnnn | nnnnnnnnnn | 10920 |
| nnnnnnnnnn | nnnnnnnnnn | nnnnnnnnnn | nnnnnnnnnn | nnnnnnnnnn | nnnnnnnnnn | 10980 |
| nnnnnnnnnn | nnnnnnnnnn | nnnnnnnnnn | nnnnnnnnnn | nnnnnnnnnn | nnnnnnnnnn | 11040 |
| nnnnnnnnnn | nnnnnnnnnn | nnnnnnnnnn | nnnnnnnnnn | nnnnnnnnnn | nnnnnnnnnn | 11100 |
| nnnnnnnnnn | nnnnnnnnnn | nnnnnnnnnn | nnnnnnnnnn | nnnnnnnnnn | nnnnnnnnnn | 11160 |
| nnnnnnnnnn | nnnnnnnnnn | nnnnnnnnnn | nnnnnnnnnn | nnnnnnnnnn | nnnnnnnnnn | 11220 |
| nnnnnnnnnn | nnnnnnnnnn | nnnnnnnnnn | nnnnnnnnnn | nnnnnnnnnn | nnnnnnnnnn | 11280 |
| nnnnnnnnnn | nnnnnnnnnn | nnnnnnnnnn | nnnnnnnnnn | nnnnnnnnnn | nnnnnnnnnn | 11340 |
| nnnnnnnnnn | nnnnnnnnnn | nnnnnnnnnn | nnnnnnnnnn | nnnnnnnnnn | nnnnnnnnnn | 11400 |
| nnnnnnnnnn | nnnnnnnnnn | nnnnnnnnnn | nnnnnnnnnn | nnnnnnnnnn | nnnnnnnnnn | 11460 |
| nnnnnnnnnn | nnnnnnnnnn | nnnnnnnnnn | nnnnnnnnnn | nnnnnnnnnn | nnnnnnnnnn | 11520 |
| nnnnnnnnnn | nnnnnnnnnn | nnnnnnnnnn | nnnnnnnnnn | nnnnnnnnnn | nnnnnnnnnn | 11580 |
| nnnnnnnnnn | nnnnnnnnnn | nnnnnnnnnn | nnnnnnnnnn | nnnnnnnnnn | nnnnnnnnnn | 11640 |
| nnnnnnnnnn | nnnnnnnnnn | nnnnnnnnnn | nnnnnnnnnn | nnnnnnnnnn | nnnnnnnnnn | 11700 |
| nnnnnnnnnn | nnnnnnnnnn | nnnnnnnnnn | nnnnnnnnnn | nnnnnnnnnn | nnnnnnnnnn | 11760 |
| nnnnnnnnnn | nnnnnnnnnn | nnnnnnnnnn | nnnnnnnnnn | nnnnnnnnnn | nnnnnnnnnn | 11820 |
| nnnnnnnnnn | nnnnnnnnnn | nnnnnnnnnn | nnnnnnnnnn | nnnnnnnnnn | nnnnnnnnnn | 11880 |
| nnnnnnnnnn | nnnnnnnnnn | nnnnnnnnnn | nnnnnnnnnn | nnnnnnnnnn | nnnnnnnnnn | 11940 |
| nnnnnnnnnn | nnnnnnnnnn | nnnnnnnnnn | nnnnnnnnnn | nnnnnnnnnn | nnnnnnnnnn | 12000 |
| nnnnnnnnnn | nnnnnnnnnn | nnnnnnnnnn | nnnnnnnnnn | nnnnnnnnnn | nnnnnnnnnn | 12060 |
| nnnnnnnnnn | nnnnnnnnnn | nnnnnnnnnn | nnnnnnnnnn | nnnnnnnnnn | nnnnnnnnnn | 12120 |
| nnnnnnnnnn | nnnnnnnnnn | nnnnnnnnnn | nnnnnnnnnn | nnnnnnnnnn | nnnnnnnnnn | 12180 |
| nnnnnnnnnn | nnnnnnnnnn | nnnnnnnnnn | nnnnnnnnnn | nnnnnnnnnn | nnnnnnnnnn | 12240 |
| nnnnnnnnnn | nnnnnnnnnn | nnnnnnnnnn | nnnnnnnnnn | nnnnnnnnnn | nnnnnnnnnn | 12300 |
| nnnnnnnnnn | nnnnnnnnnn | nnnnnnnnnn | nnnnnnnnnn | nnnnnnnnnn | nnnnnnnnnn | 12360 |
| nnnnnnnnnn | nnnnnnnnnn | nnnnnnnnnn | nnnnnnnnnn | nnnnnnnnnn | nnnnnnnnnn | 12420 |
| nnnnnnnnnn | nnnnnnnnnn | nnnnnnnnnn | nnnnnnnnnn | nnnnnnnnnn | nnnnnnnnnn | 12480 |
| nnnnnnnnnn | nnnnnnnnnn | nnnnnnnnnn | nnnnnnnnnn | nnnnnnnnnn | nnnnnnnnnn | 12540 |

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 12600 |
| nnnnnnnnnn | nnnnnnnnnn | nnnnnnnnnn | nnnnnnnnnn | nnnnnnnnnn | nnnnnnnnnn | 12660 |
| nnnnnnnnnn | nnnnnnnnnn | nnnnnnnnnn | nnnnnnnnnn | nnnnnnnnnn | nnnnnnnnnn | 12720 |
| nnnnnnnnnn | nnnnnnnnnn | nnnnnnnnnn | nnnnnnnnnn | nnnnnnnnnn | nnnnnnnnnn | 12780 |
| nnnnnnnnnn | nnnnnnnnnn | nnnnnnnnnn | nnnnnnnnnn | nnnnnnnnnn | nnnnnnnnnn | 12840 |
| nnnnnnnnnn | nnnnnnnnnn | nnnnnnnnnn | nnnnnnnnnn | nnnnnnnnnn | nnnnnnnnnn | 12900 |
| nnnnnnnnnn | nnnnnnnnnn | nnnnnnnnnn | nnnnnnnnnn | nnnnnnnnnn | nnnnnnnnnn | 12960 |
| nnnnnnnnnn | nnnnnnnnnn | nnnnnnnnnn | nnnnnnnnnn | nnnnnnnnnn | nnnnnnnnnn | 13020 |
| nnnnnnnnnn | nnnnnnnnnn | nnnnnnnnnn | nnnnnnnnnn | nnnnnnnnnn | nnnnnnnnnn | 13080 |
| nnnnnnnnnn | nnnnnnnnnn | nnnnnnnnnn | nnnnnnnnnn | nnnnnnnnnn | nnnnnnnnnn | 13140 |
| nnnnnnnnnn | nnnnnnnnnn | nnnnnnnnnn | nnnnnnnnnn | nnnnnnnnnn | nnnnnnnnnn | 13200 |
| nnnnnnnnnn | nnnnnnnnnn | nnnnnnnnnn | nnnnnnnnnn | nnnnnnnnnn | nnnnnnnnnn | 13260 |
| nnnnnnnnnn | nnnnnnnnnn | nnnnnnnnnn | nnnnnnnnnn | nnnnnnnnnn | nnnnnnnnnn | 13320 |
| nnnnnnnnnn | nnnnnnnnnn | nnnnnnnnnn | nnnnnnnnnn | nnnnnnnnnn | nnnnnnnnnn | 13380 |
| nnnnnnnnnn | nnnnnnnnnn | nnnnnnnnnn | nnnnnnnnnn | nnnnnnnnnn | nnnnnnnnnn | 13440 |
| nnnnnnnnnn | nnnnnnnnnn | nnnnnnnnnn | nnnnnnnnnn | nnnnnnnnnn | nnnnnnnnnn | 13500 |
| nnnnnnnnnn | nnnnnnnnnn | nnnnnnnnnn | nnnnnnnnnn | nnnnnnnnnn | nnnnnnnnnn | 13560 |
| nnnnnnnnnn | nnnnnnnnnn | nnnnnnnnnn | nnnnnnnnnn | nnnnnnnnnn | nnnnnnnnnn | 13620 |
| nnnnnnnnnn | nnnnnnnnnn | nnnnnnnnnn | nnnnnnnnnn | nnnnnnnnnn | nnnnnnnnnn | 13680 |
| nnnnnnnnnn | nnnnnnnnnn | nnnnnnnnnn | nnnnnnnnnn | nnnnnnnnnn | nnnnnnnnnn | 13740 |
| nnnnnnnnnn | nnnnnnnnnn | nnnnnnnnnn | nnnnnnnnnn | nnnnnnnnnn | nnnnnnnnnn | 13800 |
| nnnnnnnnnn | nnnnnnnnnn | nnnnnnnnnn | nnnnnnnnnn | nnnnnnnnnn | nnnnnnnnnn | 13860 |
| nnnnnnnnnn | nnnnnnnnnn | nnnnnnnnnn | nnnnnnnnnn | nnnnnnnnnn | nnnnnnnnnn | 13920 |
| nnnnnnnnnn | nnnnnnnnnn | nnnnnnnnnn | nnnnnnnnnn | nnnnnnnnnn | nnnnnnnnnn | 13980 |
| nnnnnnnnnn | nnnnnnnnnn | nnnnnnnnnn | nnnnnnnnnn | nnnnnnnnnn | nnnnnnnnnn | 14040 |
| nnnnnnnnnn | nnnnnnnnnn | nnnnnnnnnn | nnnnnnnnnn | nnnnnnnnnn | nnnnnnnnnn | 14100 |
| nnnnnnnnnn | nnnnnnnnnn | nnnnnnnnnn | nnnnnnnnnn | nnnnnnnnnn | nnnnnnnnnn | 14160 |
| nnnnnnnnnn | nnnnnnnnnn | nnnnnnnnnn | nnnnnnnnnn | nnnnnnnnnn | nnnnnnnnnn | 14220 |
| nnnnnnnnnn | nnnnnnnnnn | nnnnnnnnnn | nnnnnnnnnn | nnnnnnnnnn | nnnnnnnnnn | 14280 |
| nnnnnnnnnn | nnnnnnnnnn | nnnnnnnnnn | nnnnnnnnnn | nnnnnnnnnn | nnnnnnnnnn | 14340 |
| nnnnnnnnnn | nnnnnnnnnn | nnnnnnnnnn | nnnnnnnnnn | nnnnnnnnnn | nnnnnnnnnn | 14400 |
| nnnnnnnnnn | nnnnnnnnnn | nnnnnnnnnn | nnnnnnnnnn | nnnnnnnnnn | nnnnnnnnnn | 14460 |
| nnnnnnnnnn | nnnnnnnnnn | nnnnnnnnnn | nnnnnnnnnn | nnnnnnnnnn | nnnnnnnnnn | 14520 |
| nnnnnnnnnn | nnnnnnnnnn | nnnnnnnnnn | nnnnnnnnnn | nnnnnnnnnn | nnnnnnnnnn | 14580 |
| nnnnnnnnnn | nnnnnnnnnn | nnnnnnnnnn | nnnnnnnnnn | nnnnnnnnnn | nnnnnnnnnn | 14640 |
| nnnnnnnnnn | nnnnnnnnnn | nnnnnnnnnn | nnnnnnnnnn | nnnnnnnnnn | nnnnnnnnnn | 14700 |
| nnnnnnnnnn | nnnnnnnnnn | nnnnnnnnnn | nnnnnnnnnn | nnnnnnnnnn | nnnnnnnnnn | 14760 |
| nnnnnnnnnn | nnnnnntttt | tgaaagctac | tagtaggtca | ccattttttc | ttgtcttccc | 14820 |
| gcaatccaga | ccagcgccac | cgcctccgac | agtgtcctcg | ctctacctct | gacctctccg | 14880 |

-continued

```
gaggttccgc tgcctccaag ccggacttag ggcttcaaga ggcgggcgtg ccctctggag      14940 tccctacca tgactgaagg cgccagagac tggcggtgtc ttaagactcc gggcaccgcc       15000
acgcgctgtc aagcaacact ctgcggacct gccggcgtag ttgcagcggg ggcttgggga     15060
ggggctgggg gttggacggg attgaggaag gtccgcacag cctgtctctg ctcagttgca     15120
ataaacgtga catcttggga gcgttcccca gagtttgtct gcttctagaa cccgggtcgc     15180
tcctgctgcg gttccaggtt tggccgccag aagacgctgc cgcctcagac gagggcgggc     15240 tgtgtgggc gggagtacca gaaagggtcg gcgtgtgtcc ccgggatgct cgcagcttcc     15300
ctctgcccag actggggtgg ctttcggcgc aatctgtcaa gctgttggac ctgccgtccc    15360
cactctgacc attggctggg aaaagtggat ctggctgatg ctcccagagc ccaggagcca    15420
gggcggagcg gggcggcggc tgctcccacg atcccaaggc cgcgcacctg cctcctcccc    15480
ctccgccgcc gccacttgag ggatcgggaa caaaggtgct ttgtacaggc cgcaaccacc    15540
tcattacttc gtcttaggga ctggggccgc gtgggccccc agcccggaac gaaggtgtgg    15600
agcggcaagg gacagacgcc aatcttaaag tgagcatcta gcgcgccacc taaggctctt    15660
tagggaaggt ggtcccagag ctgtgttgtc ccttccgctt gcactgtccc tagatgtgca    15720
aagaaaacgg ggcagtgcat gaaggtggtt ggacaggctt catggatcct cgcccgcgcc    15780
tcactttccc ctatctgggc aaaggttatg taccttatt taaaatcttc caaacttcta    15840
ataaggcagt ctaccctgca ctaaagcaga cacgaaagag atgacctccc taaaaatact    15900
gctgttggaa tacgtccttc cttcccgccc cctcgcagtg cggtgcagcc tcagtggaag    15960
ctttggcgaa cctggcgcgc gctgcggtgc acagagggtt aactggagtt ggcgctgggt    16020
ggagaggagg agacgcgctc ccattggcgg aaagttattc aggggcgggg tcagtgaatc    16080
tccgtacccc actcccctt ccgcaacttc cctcttcact ttgtaccttt ctctcctcga    16140
ctgtgaagcg ggccgggacc tgccaggcca gaccaaaccg gacctcgggg gcgatgcggc    16200
tgctgcccct gctgcggact gtcctatggg ccgcgtcctc ggctccctc tgcgcggggg     16260 ctccagcctc cgccacgtag tctactggaa ctccagtaac cccaggtagc cgggccgaac    16320
cgggcgagcg cacagccaag tctgcgcgct cccgggcttt gcgcgcgccc gccacccgct    16380 cttttgcgcgg cgccgcctga gcctggccgc gcgccggggc tcctttgttt gagcggcgg    16440 gggaggggg agggcgagg ggcgaggcgc gccctgggtc tccccacagc ccgcatgtgt     16500 tgggggcag gcagaagacc ccagccccaa gggttgtcta gggggtcttg gagcatggag    16560
ctgggggggc ctttgcccgc actccgggct ccgcccccct cgctgctctc ctggcgatcc   16620
ccagcctccc gcaggctgga gctgtggctg acgaacttga gagcgaggga gggggctta    16680 ctcttatgaa agagcgtggg ttactctcct gcccgctggg tctcacctct ggctctcact    16740
ctgtctcctg atctcatttg ctatctctgc tttcatctct gtctttattg gtccttctgt     16800
ttctttccag tgtcagccct gcccttctag ccgaatcacc tctgggcaag tctcgtgacc   16860
ttcctaacct catttatctc acctgtataa tgggctaata ataccctagta ccctgggaag    16920 tctggcaggg taagtgaggt catgtatgtg aaagaggctc aggctgtaca gatataaact    16980
attatttctt tctctctcct gagctgcctg ccttttgaacc ttagtatatt ttactgttttc    17040 catccccctc cccaagtctc cctgcctctc ctatttccta tctgttttc tttctgattt     17100 tctacttgag acaatctgtg actattcatt tcttcact                              17138
```

<210> SEQ ID NO 4
<211> LENGTH: 814

-continued

```
<212> TYPE: PRT
<213> ORGANISM: Human
<220> FEATURE:
<221> NAME/KEY: VARIANT
<222> LOCATION: (1)...(814)
<223> OTHER INFORMATION: Xaa = Any Amino Acid

<400> SEQUENCE: 4
```

| | | | | | | | | | | | | | | | |
|---|---|---|---|---|---|---|---|---|---|---|---|---|---|---|---|
| Met | Arg | Leu | Ala | Leu | Leu | Trp | Ala | Leu | Gly | Leu | Leu | Ala | Gly | Ser |
| 1 | | | | 5 | | | | | 10 | | | | | 15 |
| Pro | Leu | Pro | Ser | Trp | Pro | Leu | Pro | Asn | Ile | Gly | Gly | Thr | Glu | Glu | Gln |
| | | | 20 | | | | | 25 | | | | | 30 | | |
| Gln | Ala | Glu | Ser | Glu | Lys | Ala | Pro | Arg | Glu | Pro | Leu | Glu | Pro | Gln | Val |
| | | 35 | | | | | 40 | | | | | 45 | | | |
| Leu | Gln | Asp | Asp | Leu | Pro | Ile | Ser | Leu | Lys | Lys | Val | Leu | Gln | Thr | Ser |
| 50 | | | | | 55 | | | | | 60 | | | | | |
| Leu | Pro | Glu | Pro | Leu | Arg | Ile | Lys | Leu | Glu | Leu | Asp | Gly | Asp | Ser | His |
| 65 | | | | | 70 | | | | | 75 | | | | | 80 |
| Ile | Leu | Glu | Leu | Leu | Gln | Asn | Arg | Glu | Leu | Val | Pro | Gly | Arg | Pro | Thr |
| | | | | 85 | | | | | 90 | | | | | 95 | |
| Leu | Val | Trp | Tyr | Gln | Pro | Asp | Gly | Thr | Arg | Val | Val | Ser | Glu | Gly | His |
| | | | | 100 | | | | | 105 | | | | | 110 | |
| Thr | Leu | Glu | Asn | Cys | Cys | Tyr | Gln | Gly | Arg | Val | Arg | Gly | Tyr | Ala | Gly |
| | | | 115 | | | | | 120 | | | | | 125 | | |
| Ser | Trp | Val | Ser | Ile | Cys | Thr | Cys | Ser | Gly | Leu | Arg | Gly | Leu | Val | Val |
| | 130 | | | | | 135 | | | | | 140 | | | | |
| Leu | Thr | Pro | Glu | Arg | Ser | Tyr | Thr | Leu | Glu | Gln | Gly | Pro | Gly | Asp | Leu |
| 145 | | | | | 150 | | | | | 155 | | | | | 160 |
| Gln | Gly | Pro | Pro | Ile | Ile | Ser | Arg | Ile | Gln | Asp | Leu | His | Leu | Pro | Gly |
| | | | | 165 | | | | | 170 | | | | | 175 | |
| His | Thr | Cys | Ala | Leu | Ser | Trp | Arg | Glu | Ser | Val | His | Thr | Gln | Thr | Pro |
| | | | 180 | | | | | 185 | | | | | 190 | | |
| Pro | Glu | His | Pro | Leu | Gly | Gln | Arg | His | Ile | Arg | Arg | Arg | Arg | Asp | Val |
| | | | | 195 | | | | | 200 | | | | | 205 | |
| Val | Thr | Glu | Thr | Lys | Thr | Val | Glu | Leu | Val | Ile | Val | Ala | Asp | His | Ser |
| | 210 | | | | | 215 | | | | | 220 | | | | |
| Glu | Ala | Gln | Lys | Tyr | Arg | Asp | Phe | Gln | His | Leu | Leu | Asn | Arg | Thr | Leu |
| 225 | | | | | 230 | | | | | 235 | | | | | 240 |
| Glu | Val | Ala | Leu | Leu | Leu | Asp | Thr | Phe | Phe | Arg | Pro | Leu | Asn | Val | Arg |
| | | | | 245 | | | | | 250 | | | | | 255 | |
| Val | Ala | Leu | Val | Gly | Leu | Glu | Ala | Trp | Thr | Gln | Arg | Asp | Leu | Val | Glu |
| | | | 260 | | | | | 265 | | | | | 270 | | |
| Ile | Ser | Pro | Asn | Pro | Ala | Val | Thr | Leu | Glu | Asn | Phe | Leu | His | Trp | Arg |
| | | 275 | | | | | 280 | | | | | 285 | | | |
| Arg | Ala | His | Leu | Leu | Pro | Arg | Leu | Pro | His | Asp | Ser | Ala | Gln | Leu | Val |
| 290 | | | | | 295 | | | | | 300 | | | | | |
| Thr | Gly | Thr | Ser | Phe | Ser | Gly | Pro | Thr | Val | Gly | Met | Ala | Ile | Gln | Asn |
| 305 | | | | | 310 | | | | | 315 | | | | | 320 |
| Ser | Ile | Cys | Ser | Pro | Asp | Phe | Ser | Gly | Gly | Val | Asn | Met | Asp | His | Ser |
| | | | 325 | | | | | 330 | | | | | 335 | | |
| Thr | Ser | Ile | Leu | Gly | Val | Ala | Ser | Ile | Ala | His | Glu | Leu | Gly | His | |
| | | | 340 | | | | | 345 | | | | | 350 | | |
| Ser | Leu | Gly | Leu | Asp | His | Asp | Leu | Pro | Gly | Asn | Ser | Cys | Pro | Cys | Pro |
| | | 355 | | | | | 360 | | | | | 365 | | | |
| Gly | Pro | Ala | Pro | Ala | Lys | Thr | Cys | Ile | Met | Glu | Ala | Ser | Thr | Asp | Phe |

```
            370                 375                 380
Leu Pro Gly Leu Asn Phe Ser Asn Cys Ser Arg Arg Ala Leu Glu Lys
385                 390                 395                 400

Ala Leu Leu Asp Gly Met Gly Ser Cys Leu Phe Glu Arg Leu Pro Ser
                405                 410                 415

Leu Pro Pro Met Ala Ala Phe Cys Gly Asn Met Phe Val Glu Pro Gly
                420                 425                 430

Glu Gln Cys Asp Cys Gly Phe Leu Asp Asp Cys Val Asp Pro Cys Cys
                435                 440                 445

Asp Ser Leu Thr Cys Gln Leu Arg Pro Gly Ala Gln Cys Ala Ser Asp
                450                 455                 460

Gly Pro Cys Cys Gln Asn Cys Gln Leu Arg Pro Ser Gly Trp Gln Cys
465                 470                 475                 480

Arg Pro Thr Arg Gly Asp Cys Asp Leu Pro Glu Phe Cys Pro Gly Asp
                485                 490                 495

Ser Ser Gln Cys Pro Pro Asp Val Ser Leu Gly Asp Gly Glu Pro Cys
                500                 505                 510

Ala Gly Gly Gln Ala Val Cys Met His Gly Arg Cys Ala Ser Tyr Ala
                515                 520                 525

Gln Gln Cys Gln Ser Leu Trp Gly Pro Gly Ala Gln Pro Ala Ala Pro
                530                 535                 540

Leu Cys Leu Gln Thr Ala Asn Thr Arg Gly Asn Ala Phe Gly Ser Cys
545                 550                 555                 560

Gly Arg Asn Pro Ser Gly Ser Tyr Val Ser Cys Thr Pro Arg Asp Ala
                565                 570                 575

Ile Cys Gly Gln Leu Gln Cys Gln Thr Gly Arg Thr Gln Pro Leu Leu
                580                 585                 590

Gly Ser Ile Arg Asp Leu Leu Trp Glu Thr Ile Asp Val Asn Gly Thr
                595                 600                 605

Glu Leu Asn Cys Ser Trp Val His Leu Asp Leu Gly Ser Asp Val Ala
                610                 615                 620

Gln Pro Leu Leu Thr Leu Pro Gly Thr Ala Cys Gly Pro Gly Leu Val
625                 630                 635                 640

Cys Ile Asp His Arg Cys Gln Arg Val Asp Leu Leu Gly Ala Gln Glu
                645                 650                 655

Cys Arg Ser Lys Cys His Gly His Gly Val Cys Asp Ser Asn Arg His
                660                 665                 670

Cys Tyr Cys Glu Glu Gly Trp Ala Pro Pro Asp Cys Thr Thr Gln Leu
                675                 680                 685

Lys Ala Thr Ser Ser Leu Thr Thr Gly Leu Leu Leu Ser Leu Leu Val
                690                 695                 700

Leu Leu Val Leu Val Met Leu Gly Ala Ser Tyr Trp Tyr Arg Ala Arg
705                 710                 715                 720

Leu Xaa Gln Arg Leu Cys Gln Leu Lys Gly Pro Thr Cys Gln Tyr Arg
                725                 730                 735

Ala Ala Gln Ser Gly Pro Ser Glu Arg Pro Gly Pro Pro Gln Arg Ala
                740                 745                 750

Leu Leu Ala Arg Gly Thr Lys Ser Gln Gly Pro Ala Lys Pro Pro Pro
                755                 760                 765

Pro Arg Lys Pro Leu Pro Ala Asp Pro Gln Gly Arg Cys Pro Ser Gly
                770                 775                 780

Asp Leu Pro Gly Pro Gly Pro Gly Ile Pro Pro Leu Val Val Pro Ser
785                 790                 795                 800
```

-continued

```
Arg Pro Ala Pro Pro Pro Pro Thr Val Ser Ser Leu Tyr Leu
            805                 810
```